US012595262B2

(12) United States Patent
Machacek et al.

(10) Patent No.: US 12,595,262 B2
(45) **Date of Patent: *Apr. 7, 2026**

(54) PRMT5 INHIBITORS

(71) Applicant: MERCK SHARP & DOHME LLC, Rahway, NJ (US)

(72) Inventors: Michelle Machacek, Boston, MA (US); Michael D. Altman, Boston, MA (US); Chunhui Huang, Boston, MA (US); Michael H. Reutershan, Boston, MA (US); David L. Sloman, Boston, MA (US); David J. Witter, Toronto (CA); Craig R. Gibeau, Boston, MA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 772 days.

This patent is subject to a terminal disclaimer.

(21) Appl. No.: 17/787,113

(22) PCT Filed: Dec. 14, 2020

(86) PCT No.: PCT/US2020/064765
§ 371 (c)(1),
(2) Date: Jun. 17, 2022

(87) PCT Pub. No.: WO2021/126731
PCT Pub. Date: Jun. 24, 2021

(65) Prior Publication Data

US 2023/0108452 A1 Apr. 6, 2023

Related U.S. Application Data

(60) Provisional application No. 63/025,629, filed on May 15, 2020, provisional application No. 62/949,242,
(Continued)

(51) Int. Cl.
*C07D 487/04* (2006.01)
*C07D 401/14* (2006.01)

(52) U.S. Cl.
CPC ......... *C07D 487/04* (2013.01); *C07D 401/14* (2013.01); *C07B 2200/05* (2013.01)

(58) Field of Classification Search
CPC .. C07D 487/04; C07D 401/14; C07B 2200/05
(Continued)

(56) References Cited

U.S. PATENT DOCUMENTS 2,789,118 A 4/1957 Seymour
2,990,401 A 6/1961 Seymour
(Continued)

FOREIGN PATENT DOCUMENTS

CN 108570059 A 9/2018
WO 1994015932 A1 7/1994
(Continued)

OTHER PUBLICATIONS

Aggarwal et al., Nuclear Cyclin D1/CDK4 Kinase Regulates CUL4 Expression and Triggers Neoplastic Growth via Activation of the PRMT5 Methyltransferase, Cancer Cell 2010, 18, 329-340.
(Continued)

*Primary Examiner* — Jeffrey S Lundgren
*Assistant Examiner* — Heather Dahlin
(74) *Attorney, Agent, or Firm* — Stites & Harbison PLLC; Richard S. Myers, Jr.

(57) ABSTRACT

The present invention provides a compound selected from: compounds A, B, C, D and the pharmaceutically acceptable salts, esters, and prodrugs thereof, which are PRMT5 inhibitors. Also provided are methods of making compounds disclosed herein, pharmaceutical compositions comprising compounds disclosed herein, and methods of using these compounds to treat cancer, sickle cell, and hereditary persistence of foetal hemoglobin (HPFH) mutations.

(A)

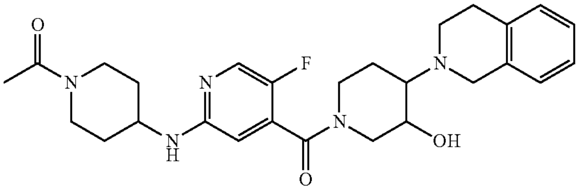

(B)

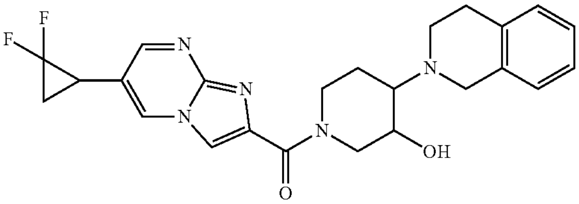

(C)

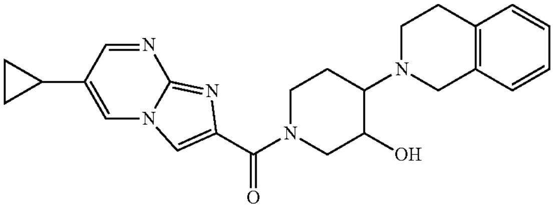

(Continued)

-continued (D)

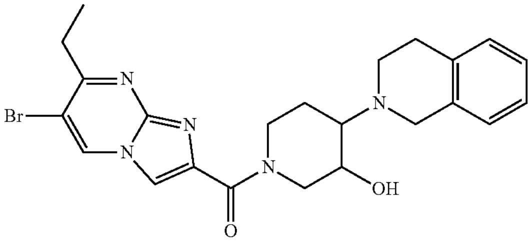

14 Claims, No Drawings

Related U.S. Application Data filed on Dec. 17, 2019, provisional application No. 62/949,248, filed on Dec. 17, 2019.

(58) Field of Classification Search
USPC .......................................................... 514/259.1
See application file for complete search history.

(56) References Cited

U.S. PATENT DOCUMENTS

| | | | |
|---|---|---|---|
| 3,048,581 | A | 8/1962 | Josef |
| 3,126,375 | A | 3/1964 | Hensel et al. |
| 3,749,712 | A | 7/1973 | Cavazza |
| 3,928,326 | A | 12/1975 | Brattsand |
| 3,929,768 | A | 12/1975 | Brattsand |
| 3,996,359 | A | 12/1976 | Brattsand |
| 4,231,938 | A | 11/1980 | Monaghan et al. |
| 4,294,926 | A | 10/1981 | Monaghan et al. |
| 4,319,039 | A | 3/1982 | Albers-schonberg |
| 4,346,227 | A | 8/1982 | Terahara et al. |
| 4,410,629 | A | 10/1983 | Terahara et al. |
| 4,444,784 | A | 4/1984 | Hoffman et al. |
| 4,537,859 | A | 8/1985 | Terahara et al. |
| 4,681,893 | A | 7/1987 | Roth |
| 4,782,084 | A | 11/1988 | Vyas et al. |
| 4,820,850 | A | 4/1989 | Verhoeven et al. |
| 4,885,314 | A | 12/1989 | Vyas |
| 4,911,165 | A | 3/1990 | Lennard et al. |
| 4,916,239 | A | 4/1990 | Treiber |
| 4,929,437 | A | 5/1990 | Tobert |
| 5,030,447 | A | 7/1991 | Joshi et al. |
| 5,118,853 | A | 6/1992 | Lee et al. |
| 5,134,142 | A | 7/1992 | Matsuo et al. |
| 5,177,080 | A | 1/1993 | Angerbauer et al. |
| 5,180,589 | A | 1/1993 | Joshi et al. |
| 5,189,164 | A | 2/1993 | Kapa et al. |
| 5,273,995 | A | 12/1993 | Roth |
| 5,290,946 | A | 3/1994 | Lee et al. |
| 5,342,952 | A | 8/1994 | Butler et al. |
| 5,344,991 | A | 9/1994 | Reitz et al. |
| 5,354,772 | A | 10/1994 | Kathawala |
| 5,356,896 | A | 10/1994 | Kabadi et al. |
| 5,393,790 | A | 2/1995 | Reitz et al. |
| 5,409,944 | A | 4/1995 | Black et al. |
| 5,436,265 | A | 7/1995 | Black et al. |
| 5,466,823 | A | 11/1995 | Talley et al. |
| 5,474,995 | A | 12/1995 | Ducharme et al. |
| 5,489,691 | A | 2/1996 | Butler et al. |
| 5,536,752 | A | 7/1996 | Ducharme et al. |
| 5,550,142 | A | 8/1996 | Ducharme et al. |
| 5,604,260 | A | 2/1997 | Guay et al. |
| 5,633,272 | A | 5/1997 | Talley et al. |
| 5,698,584 | A | 12/1997 | Black et al. |
| 5,710,140 | A | 1/1998 | Ducharme et al. |
| 5,861,419 | A | 1/1999 | Dube et al. |
| 5,932,598 | A | 8/1999 | Talley et al. |
| 6,001,843 | A | 12/1999 | Dube et al. |
| 6,020,343 | A | 2/2000 | Belley et al. |
| 6,069,134 | A | 5/2000 | Roth et al. |
| RE37,314 | E | 8/2001 | Hirai et al. |
| 6,284,781 | B1 | 9/2001 | Danishefsky et al. |
| 6,288,237 | B1 | 9/2001 | Hoefle et al. |
| 7,454,431 | B2 | 11/2008 | Vo et al. |
| 7,589,068 | B2 | 9/2009 | Cosford et al. |
| 7,655,675 | B2 | 2/2010 | Nadin et al. |
| 8,785,486 | B2 | 7/2014 | Trabanco-Suarez et al. |
| 2004/0102360 | A1 | 5/2004 | Barnett et al. |
| 2004/0116432 | A1 | 6/2004 | Carling et al. |
| 2005/0176776 | A1 | 8/2005 | Coleman et al. |
| 2005/0222138 | A1 | 10/2005 | Ohhata et al. |
| 2010/0055090 | A1 | 3/2010 | Shipps, Jr. et al. |
| 2017/0298075 | A1 | 10/2017 | Bergman et al. |
| 2018/0155343 | A1 | 6/2018 | Almansa-Rosales |
| 2019/0343826 | A1 | 11/2019 | Duncan et al. |
| 2023/0108452 | A1 | 4/2023 | Machacek et al. |

FOREIGN PATENT DOCUMENTS

| | | | |
|---|---|---|---|
| WO | WO1997004785 | A1 | 2/1997 |
| WO | WO1997017070 | A1 | 5/1997 |
| WO | WO1997018813 | A1 | 5/1997 |
| WO | WO1997021701 | A1 | 6/1997 |
| WO | WO1997023478 | A1 | 7/1997 |
| WO | WO1997026246 | A1 | 7/1997 |
| WO | WO1997030053 | A1 | 8/1997 |
| WO | WO1997038665 | A2 | 10/1997 |
| WO | WO1997044350 | A1 | 11/1997 |
| WO | WO1998002436 | A1 | 1/1998 |
| WO | WO1998028980 | A1 | 7/1998 |
| WO | WO1998029119 | A1 | 7/1998 |
| WO | WO2000000472 | A1 | 1/2000 |
| WO | 0050032 | A1 | 8/2000 |
| WO | 200044777 | A1 | 8/2000 |
| WO | 200061186 | A1 | 10/2000 |
| WO | 2001070677 | A1 | 9/2001 |
| WO | 2001090084 | A1 | 11/2001 |
| WO | 2002030912 | A1 | 4/2002 |
| WO | 2002036555 | A1 | 5/2002 |
| WO | 2002047671 | A2 | 6/2002 |
| WO | 2002081433 | A1 | 10/2002 |
| WO | 2002081435 | A1 | 10/2002 |
| WO | 2002083064 | A2 | 10/2002 |
| WO | 2002083138 | A1 | 10/2002 |
| WO | 2002083139 | A1 | 10/2002 |
| WO | 2002083140 | A1 | 10/2002 |
| WO | 2003013506 | A1 | 2/2003 |
| WO | 2003018543 | A1 | 3/2003 |
| WO | 2003039460 | A2 | 5/2003 |
| WO | 2003049527 | A2 | 6/2003 |
| WO | 2003049678 | A2 | 6/2003 |
| WO | 2003049679 | A2 | 6/2003 |
| WO | 2003050064 | A2 | 6/2003 |
| WO | 2003050122 | A2 | 6/2003 |
| WO | 2003079973 | A2 | 10/2003 |
| WO | 2003084473 | A2 | 10/2003 |
| WO | 2003086279 | A2 | 10/2003 |
| WO | 2003086394 | A1 | 10/2003 |
| WO | 2003086403 | A1 | 10/2003 |
| WO | 2003086404 | A1 | 10/2003 |
| WO | 2003093251 | A1 | 11/2003 |
| WO | 2003093252 | A1 | 11/2003 |
| WO | 2003093253 | A1 | 11/2003 |
| WO | 2003093264 | A1 | 11/2003 |
| WO | 2003099211 | A2 | 12/2003 |
| WO | 2003105855 | A1 | 12/2003 |
| WO | 2003106417 | A1 | 12/2003 |
| WO | 2004031137 | A1 | 4/2004 |
| WO | 2004031138 | A1 | 4/2004 |
| WO | 2004031139 | A1 | 4/2004 |
| WO | 2004037171 | A2 | 5/2004 |
| WO | 2004039370 | A1 | 5/2004 |
| WO | 2004039774 | A2 | 5/2004 |
| WO | 2004039800 | A1 | 5/2004 |

(56) References Cited

FOREIGN PATENT DOCUMENTS

| | | | |
|---|---|---|---|
| WO | 2004041162 | A2 | 5/2004 |
| WO | 2004058148 | A2 | 7/2004 |
| WO | 2004058700 | A2 | 7/2004 |
| WO | 2004089911 | A1 | 10/2004 |
| WO | 2004096129 | A2 | 11/2004 |
| WO | 2004096130 | A2 | 11/2004 |
| WO | 2004096131 | A2 | 11/2004 |
| WO | WO2004096135 | A2 | 11/2004 |
| WO | WO2004101538 | A1 | 11/2004 |
| WO | WO2004101539 | A1 | 2/2005 |
| WO | WO2005014553 | A1 | 2/2005 |
| WO | WO2005017190 | A2 | 2/2005 |
| WO | WO2005018547 | A2 | 3/2005 |
| WO | WO2005018638 | A1 | 3/2005 |
| WO | WO2005019205 | A1 | 3/2005 |
| WO | WO2005019206 | A1 | 3/2005 |
| WO | WO2005030731 | A1 | 4/2005 |
| WO | WO2005100344 | A1 | 10/2005 |
| WO | WO2005100356 | A1 | 10/2005 |
| WO | WO2012087861 | A1 | 6/2012 |
| WO | WO2013/000909 | A1 | 1/2013 |
| WO | WO2014100719 | A2 | 6/2014 |
| WO | WO2017032840 | A1 | 3/2017 |
| WO | 2018167269 | A1 | 9/2018 |
| WO | WO2019002074 | A1 | 1/2019 |
| WO | WO2019094311 | A1 | 5/2019 |
| WO | WO2019094312 | A1 | 5/2019 |
| WO | WO2019102494 | A1 | 5/2019 |
| WO | WO2020182018 | A1 | 9/2020 |

OTHER PUBLICATIONS

Chen et al., Epigenetic changes during disease progression in a murine model of human chronic lymphocytic leukemia, Proc. Natl. Acad. Sci. USA 2009, 106, 13433-13438.
Chiang et al., 2017, PRMT5 Is a Critical Regulator of Breast Cancer Stem Cell Function via Histone Methylation and FOXP1 Expression, Cell Reports 21, 3498-3513.
Cho et al., Arginine methylation controls growth regulation by E2F-1, EMBO J. 2012, 31, 1785-1797.
Clarke et al., PRMT5-Dependent Methylation of the TIP60 Coactivator RUVBL1 Is a Key Regulator of Homologous Recombination, 2017, Molecular Cell 65, 900-916.
Gerhart et al., Activation of the p53-MDM4 regulatory axis defines the antitumour response to PRMT5 inhibition through its role in regulating cellular splicing, 2018, Sci Report 8:9711.
Gu et al., Protein arginine methyltransferase 5 is essential for growth of lung cancer cells, Biochem. J. 2012, 446, 235-241.
Tamard et al., PRMT5 Regulates DNA Repair by Controlling the Alternative Splicing of Histone-Modifying Enzymes, 2018, Cell Reports 24, 2643-2657.
He Y et al., Induction of human fetal hemoglobin expression by adenosine-2',3'-dialdehyde, J. Transl. Med. 2013, 11:14.
Kanduri et al., Differential genome-wide array-based methylation profiles in prognostic subsets of chronic lymphocytic leukemia, Blood 2010, 115, 296-305.
Kim et al., Identification of Gastric Cancer-Related Genes Using a cDNA Microarray Containing Novel Expressed Sequence Tags Expressed in Gastric Cancer Cells Clin. Cancer Res. 2005, 11, 473-482.
Nicholas et al., Cancer Res. 2012, 72(8), Supplement, DOI : 10.1158/1538-7445.AM2012-LB-254.
Pal et al., Low levels of miR-92b/96 induce PRMT5 translation and H3R8/H4R3 methylation in mantle cell lymphoma, EMBO J. 2007, 26, 3558-3569.
Pollack et al., The Human Homologue of the Yeast Proteins Skb1 and Hsl7p Interacts with Jak Kinases and Contains Protein Methyltransferase Activity, J. Biol. Chem. 1999, 274, 31531-31542.
Powers et al., Protein Arginine Methyltransferase 5 Accelerates Tumor Growth by Arginine Methylation of the Tumor Suppressor Programmed Cell Death 4, Cancer Res. 2011, 71, 5579-5588.
Rank et al., Identification of a PRMT5-dependent repressor complex linked to silencing of human fetal globin gene expression, Blood 2010, 116, 1585-1592.
Wang et al., Protein Arginine Methyltransferase 5 Suppresses the Transcription of the RB Family of Tumor Suppressors in Leukemia and Lymphoma Cells, Mol. Cell Biol. 2008, 28, 6262-6277.
Zhongping et al., Protein Arginine Methyltransferase 5 Functions in Opposite Ways in the Cytoplasm and Nucleus of Prostate Cancer Cells, PLoS One 2012, 7(8): e44033.
Ben-Av et al., Induction of Vascular Endothielial Growth Factor Expression in Synovial fibroblasts by Prostaglandin E and Interleukin-1: A Potential mechanism for Inflammatory Angiogenesis, FEBS Letters, 372, 83-87, 1995.
Benezra et al., In Vivo Angiogenic Activity of Interleukins, Arch Ophthalmol, 108, 573-576, 1990.
Blume-Jensen, Peter et al., Oncogenic kinase signalling, Nature, 411, 355-365, 2001.
Bouma et al., Thrombin Activable Fibrinolysis Inhibitor (TAFI, Plasma Procarboxypeptidedase B, Procarboxypeptidase R, Procarboxypeptidase U), Thrombosis Research, 101, 329-354, 2001.
Brower, Tumor Angiogenesis New Drugs on the Block, Nature America, 17, 963-968, 1999.
Chakraborty et al., Developmental Expression of the Cyclo-Oxygenase-1 and Cyclo-oxygenase-2 genes in the Peri-implantation Mouse Uterus and their differential regulation by the blastocyst and ovarian steroids, J. Mol Endocrinol, 16, 107-122, 1996.
Chiarugi et al., Cox-2, iNOS and p53 as play-makers of tumor angiogenesis (Review), International J. of Molecular Medicine, 2, 715-719, 1998.
Diaz-Flores et al., Intense Vascular Sprouting From Rat Femoral Vein Induced by Prostaglandins E1 and E2, The Anatomical Record, 238, 68-76, 1994.
Fathallah-Shaykh et al., Gene Transfer of IFN-y into Established Brain Tumors Represses Grwoth by Antiangiogenesis, J. of Immunology, 164, 217-222, 2000.
Fernandez et al., Neovascularization Produced by Angiotensin II, Clinical Mediicne, 105, 141-145, 1985.
Gralinkski et al., Effects of Troglitazone and Pioglitazone on Cytokine-Mediated Endothelial Cell Proliferation in Vitro, J. of Cardiovascular Pharmacology, 31, 909-913, 1998.
Gu et al., Effect of Novel CAAX Peptidomimetic Farnesyltransferase Inhibitor on Angiogenesis In Vitro and In Vivo, European J. of Cancer, 35, 1394-1401, 1999.
Hall et al., The Promise and Reality of Cancer Gene Therapy, Am. J. Hum. Genet, 61, 785-789, 1997.
Harada et al., Expression and Regulation of Vascular Endothelial Growth Factor in Osteoblasts, Clinical Ortho, 313, 76-80, 1995.
Hla et al., Human Cyclooxygenase-2 cDNA, Proc. Natl. Acad. Sci., 89, 7384-7388, 1992.
Kim et al., Inhibition of Endothelial Growth Factor-Induced Angiogenesis Suppreses Tumour Growth in Vivo, Nature, 362, 841-844, 1993.
Kim, A. Y. et al., Gastric cancer by multidetector row CT: preoperative staging, Abdom Imaging, 30, 465-472, 2005.
Korte et al., Changes of the Coagulation and Fibrinolysis System n Malignancy: Their possible Impact on Future Diagnostic and Therapeutic Procedures, Clin Chem Lab Med, 38 (8), 679-692, 2000, 38.
Kufe et al., Principles of Gene Therapy, Cancer Medicine, 5th Ed., pp. 876-889, 2000.
Li et al., Adenovirus-Mediated Delivery of a uPA/uPAR Antagonist Suppresses Angiogenesis—Dependent Tumor Growth and Dissemination in Mice, Gene Therapy, 5, 1105-1113, 1998.
Majima et al., Significant Roles of Inducible Cyclooxygenase (COX)-2 in Angiogenesis in Rat Sponge Implants, Jpn. J. Pharmacol., 75, 105-114, 1997.
Miller et al., Histone Deacetylase Inhibitors, J. of Medicinal Chemistry, 46, 5097-5116, 2003.
Murata et al., Peroxisome Proliferator-Activated Receptor-y Ligands Inhibit Choroidal Neovascularization, Inestigative Ophthalmology & visual Science, 41, 2309-2317, 2000.
Murata et al., Response of Experimental Retinal Neovascularization to Thiazolidinediones, Arch Ophthamol, 119, 709-717, 2001.

(56) References Cited

OTHER PUBLICATIONS

Pubchem, SID 230731034, Available Date: Feb. 12, 2015 [retrieved on Mar. 2, 2021]. Retrieved from the Internet URL: https://pubchem.ncbi.nlm.nih.gov/substance/230731034entire document (8 pages).
PUBCHEM-SID: 337380882 Deposit Date: Jun. 18, 2017 (Jun. 18, 2017) pp. 1-7; p. 2, structure (7 pages).
Seed et al., The Inhibition of Colon-26 Adenocarcinoma Development and Angiogenesis by Topical Diclofenac in 2.5% Hyaluronan, Cancer Research, 57, 1625-1629, 1997.
Tsujii et al., Cyclooxgenase Regulates Angiogenesis Induced by Colon Cancer Cells, Cell, 93, 705-716, 1998.
Xin et al., Peroxisome Proliferator Activated Receptor y Ligands are Potent Inhibitors of Angiogenesis in Vitro and in Vivo, J. Biol Chem,, 13, 9116-9121, 1999.
Yalpani et al., Coronary Heart Disease is the most Serious Threat to life in the Western World, but Progress is Being Made in Finding Ways to Reduce the Risks of Suffering Such a Fate, Chemistry & Industry, 85-89, 1996.
Zacharski et al., Heparin and Cancer, Thromb Haemost, 80, 10-23, 1998.
Ziche et al., Role of Prostaglandin E, and Copper in Angiogenesis, JNCI, 69, 475-482, 1982.

PRMT5 INHIBITORS

CROSS REFERENCE TO RELATED APPLICATIONS

This application is a § 371 National Stage Application of PCT/US2020/064765 filed Dec. 14, 2020, which claims priority to U.S. Application No. 62/949,248 filed Dec. 17, 2019, U.S. Application No. 62,949,242 filed Dec. 17, 2019, and U.S. Application No. 63/025,629 filed May 15, 2020.

BACKGROUND OF THE INVENTION

PRMT5 (aka JBP1, SKB1, IBP72, SKB1his and HRMTIL5) is a Type II arginine methyltransferase, and was first identified in a two-hybrid search for proteins interacting with the Janus tyrosine kinase (Jak2) (Pollack et al., 1999). PRMT5 plays a significant role in control and modulation of gene transcription. Inter alia, PRMT5 is known to symmetrically methylate histone H3 at Arg-8 (a site distinct from that methylated by PRMT4) and histone H4 at Arg-3 (the same site methylated by PRMT1). PRMT5 has been reported to perform diverse roles including but not limited to impacting cell viability, stemness, DNA damage repair and RNA splicing (Clarke et al., Mol Cell (2017), Chiang et al., Cell Rep (2017), Gerhart et al., Sci Rep (2018)). Specifically, inhibition of PRMT5 induces alternative splicing of the negative regulator of p53, MDM4 resulting in increased expression of the short isoform of MDM4 (MDM4-S), decreased expression of the full-length isoform (MDM4-FL) and increased p53 activity (Gerhart el al Sci Rep (2018)). Most of the physiological functions of p53 are attributable to its role as a transcriptional activator, responding to agents that damage DNA. p53 status is wild type in approximately half of human cancer cases. These include 94% in cervix, 87% in blood malignancies, 85% in bones and endocrine glands, and 75% of primary breast cancer. Restoration of p53 in cancer cells harboring wild type p53, by way of inhibiting mechanisms that suppress its function leads to growth arrest and apoptosis and is regarded as a potentially effective means of tumor suppression.

In response to DNA damage caused by a variety of agents, including doxorubicin, camptothecin and UV light, and also in response to treatment with Nutlin-3, knockdown of PRMT5 results in an increase in sub-G1 population and concomitant reduction in G1 cells and, in the presence of p53, a significant increase in apoptosis. Knockdown of PRMT5 also resulted in an increased level of p21, a key p53 target gene that regulates cell cycle arrest during the p53 response and MDM2, a p53 E3 ubiquitin ligase, but not PUMA, NOXA, AlP1 & APAF1, p53 target genes linked to apoptosis.

Knockdown of PRMT5 (but not PRMT1 or CARM1/PRMT4) results in decreased p53 stabilization, decreased basal p53 levels, decreased p53 oligomerisation, and also decreased expression of elF4E a major component of translational machinery involved in ribosome binding to mRNA. Indeed, elF4E is a potent oncogene, which has been shown to promote malignant transformation in vitro and human cancer formation.

The role of PRMT5 in the DNA damage response has been explored with groups reporting a role for PRMT5 in regulating high fidelity holomlogous recombination mediated DNA repair in both solid (Clarke et al., Mol Cell (2017)) and hematological tumor models (Hamard et al., Cell Rep (2018)).

PRMT5 is aberrantly expressed in around half of human cancer cases, further linking this mechanism to cancers. PRMT5 overexpression has been observed in patient tissue samples and cell lines of Prostate cancer (Gu et al., 2012), Lung cancer (Zhongping et al., 2012), Melanoma cancer (Nicholas et al., 2012), Breast cancer (Powers et al., 2011), Colorectal cancer (Cho et al., 2012), Gastric cancer (Kim et al., 2005), Esophagus and Lung carcinoma (Aggarwal et al., 2010) and B-Cell lymphomas and leukemia (Wang, 2008). Moreover, elevated expression of PRMT5 in Melanoma, Breast and Colorectal cancers has been demonstrated to correlate with a poor prognosis.

Lymphoid malignancies including chronic lymphocytic leukemia (CLL) are associated with over-expression of PRMT5. PRMT5 is over-expressed (at the protein level) in the nucleus and cytosol in a number of patient derived Burkitt's lymphoma; mantle cell lymphoma (MCL); in vitro EBV-transformed lymphoma; leukemia cell lines; and B-CLL cell lines, relative to normal CD19+B lymphocytes (Pal et al., 2007; Wang et al., 2008). Intriguingly, despite elevated levels of PRMT5 protein in these tumor cells, the levels of PRMT5 mRNA are reduced (by a factor of 2-5). Translation of PRMT5 mRNA is, however, enhanced in lymphoma cells, resulting in increased levels of PRMT5 (Pal et al., 2007; Wang et al., 2008).

In addition to genomic changes, CLL, like almost all cancers, has aberrant epigenetic abnormalities characterised by global hypomethylation and hot-spots of repressive hypermethylation of promoters including tumor suppressor genes. While the role of epigenetics in the origin and progression of CLL remains unclear, epigenetic changes appear to occur early in the disease and specific patterns of DNA methylation are associated with worse prognosis (Chen et al., 2009; Kanduri et al., 2010). Global symmetric methylation of histones H3R8 and H4R3 is increased in transformed lymphoid cell lines and MCL clinical samples (Pal et al., 2007), correlating with the overexpression of PRMT5 observed in a wide variety of lymphoid cancer cell lines and MCL clinical samples.

PRMT5 is therefore a target for the identification of novel cancer therapeutics.

Hemoglobin is a major protein in red blood cells and is essential for the transport of oxygen from the lungs to the tissues. In adult humans, the most common hemoglobin type is a tetramer called hemoglobin A, consisting of two α and two β subunits. In human infants, the hemoglobin molecule is made up of two α and two γ chains. The gamma chains are gradually replaced by β subunits as the infant grows. The developmental switch in human ß-like globin gene subtype from foetal (γ) to adult (ß) that begins at birth heralds the onset of the hemoglobinopathies ß-thalassemia or sickle cell disease (SCD). In ß-thalassemia the adult chains are not produced. In SCD, a point mutation in the coding sequence in the ß globin gene leads to the production of a protein with altered polymerisation properties. The observation that increased adult γ-globin gene expression (in the setting of hereditary persistence of foetal hemoglobin (HPFH) mutations) significantly ameliorates the clinical severity of ß-thalassemia and SCD has prompted the search for therapeutic strategies to reverse γ-globin gene silencing. To date, this has been achieved through pharmacological induction, using compounds that broadly influence epigenetic modifications, including DNA methylation and histone deacetylation. The development of more targeted therapies is dependent on the identification of the molecular mechanisms underpinning foetal globin gene silencing. These mechanisms have remained elusive, despite exhaustive study of the HPFH mutations, and considerable progress in many other aspects of globin gene regulation.

PRMT5 plays a critical role in triggering coordinated repressive epigenetic events that initiate with dimethylation of histone H4 Arginine 3 (H4R3me2s), and culminate in DNA methylation and transcriptional silencing of the γ-genes (Rank et al., 2010). Integral to the synchronous establishment of the repressive markers is the assembly of a PRMT5-dependent complex containing the DNA methyltransferase DNMT3A, and other repressor proteins (Rank et al., 2010). DNMT3A is directly recruited to bind to the PRMT5-induced H4R3me2s mark, and loss of this mark through shRNA-mediated knock-down of PRMT5, or enforced expression of a mutant form of PRMT5 lacking methyltransferase activity leads to marked upregulation of γ-gene expression, and complete abrogation of DNA methylation at the γ-promoter. Treatment of human erythroid progenitors with non-specific methyltransferase inhibitors (Adox and MTA) also resulted in upregulation of γ-gene expression (He Y, 2013). Inhibitors of PRMT5 thus have potential as therapeutics for hemoglobinopathies such as ß-thalassemia or Sickle Cell Disease (SCD).

The present inventors have developed compounds that inhibit the activity of PRMT5 and therefore may be of use in treating conditions ameliorated by the inhibition of the activity of PRMT5.

SUMMARY OF THE INVENTION

The present invention provides a compound selected from:

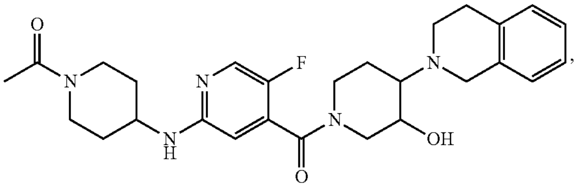 [SMILES: CC(=O)N1CCC(Nc2cc(C(=O)N3CCC(N4CCc5ccccc5C4)C(O)C3)c(F)cn2)CC1]

,

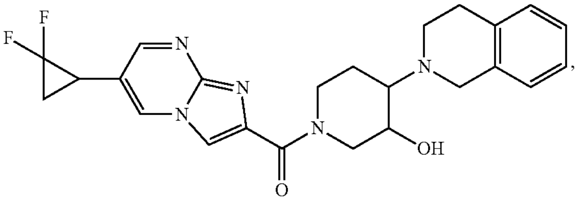

,

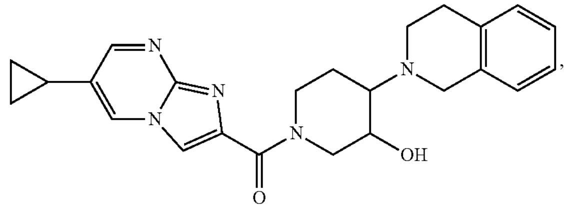

,

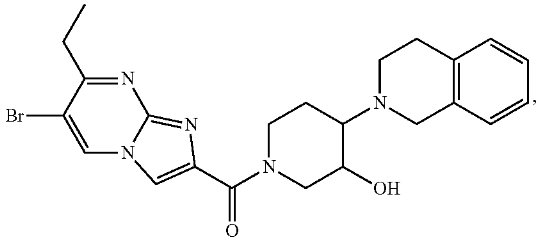

, and the pharmaceutically acceptable salts, esters, and prodrugs thereof, which are PRMT5 inhibitors. Also provided are methods of making compounds disclosed herein, pharmaceutical compositions comprising compounds disclosed herein, and methods of using these compounds to treat cancer, sickle cell, and hereditary persistence of foetal hemoglobin (HPFH) mutations.

DETAILED DESCRIPTION OF THE INVENTION

The present invention provides a compound selected from:

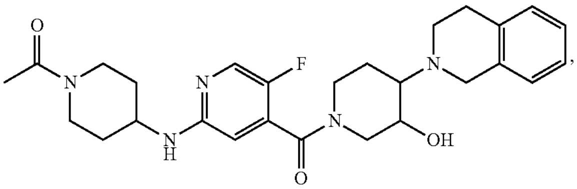

,

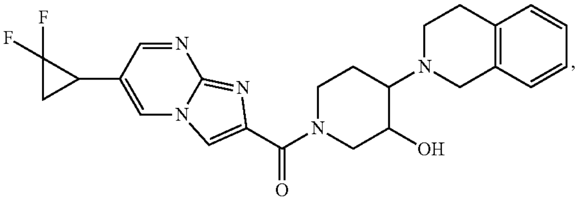

,

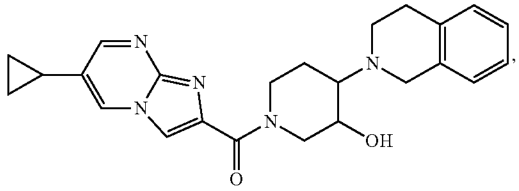

, and

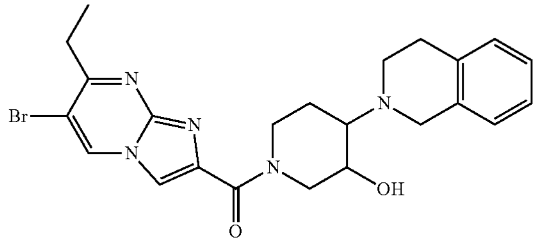

, or a pharmaceutically acceptable salt thereof.

In one embodiment, the present invention provides a compound selected from:

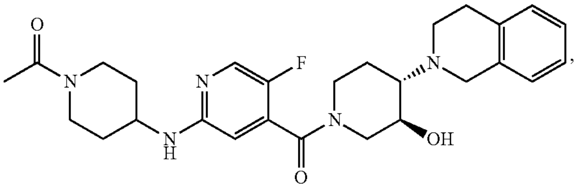

,

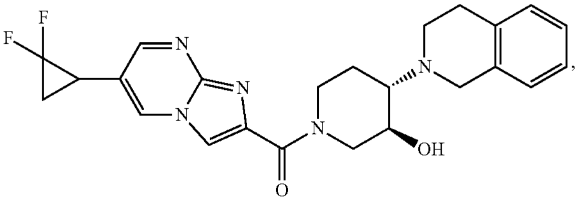

,

-continued

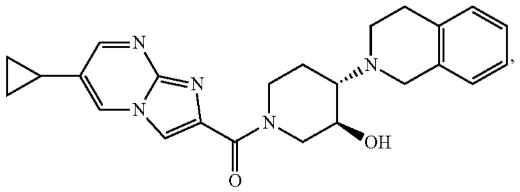

and

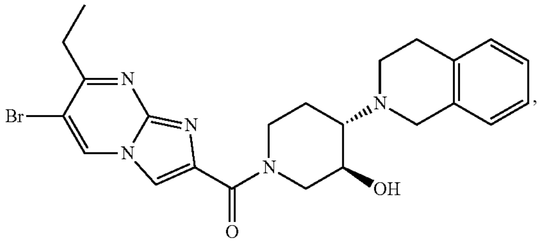

or a pharmaceutically acceptable salt thereof.

In an embodiment of the invention, the compound is,

1-{4-[(4-{[(3S,4S)-4-(3,4-dihydroisoquinolin-2(1H)-yl)-3-hydroxypiperidin-1-yl]carbonyl}-5-fluoropyridin-2-yl)amino]piperidin-1-yl}ethanone, (6-(2,2-difluorocyclopropyl)imidazo[1,2-a]pyrimidin-2-yl)((3S,4S)-4-(3,4-dihydroisoquinolin-2(1H)-yl)-3-hydroxypiperidin-1-yl)methanone, (6-cyclopropylimidazo[1,2-a]pyrimidin-2-yl)((3S,4S)-4-(3,4-dihydroisoquinolin-2(1H)-yl)-3-hydroxypiperidin-1-yl)methanone, (6-bromo-7-ethylimidazo[1,2-a]pyrimidin-2-yl)((3S,4S)-4-(3,4-dihydroisoquinolin-2(1H)-yl)-3-hydroxypiperidin-1-yl)methanone, or a pharmaceutically acceptable salt thereof.

In an embodiment of the invention, the compound is,

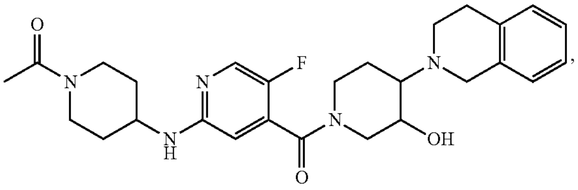

or a pharmaceutically acceptable salt thereof.

In an embodiment of the invention, the compound is,

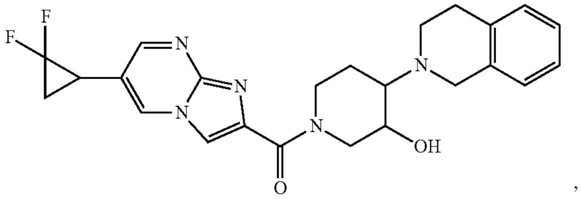 [SMILES: O=C(c1cn2cc(C3CC3(F)F)cnc2n1)N1CCC(N2CCc3ccccc3C2)C(O)C1]

or a pharmaceutically acceptable salt thereof.

In an embodiment of the invention, the compound is,

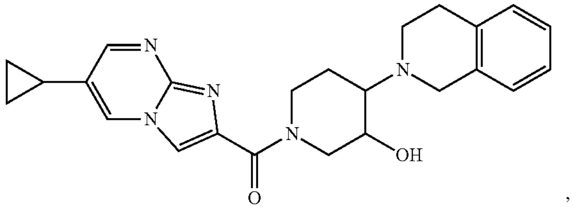 [SMILES: O=C(c1cn2cc(C3CC3)cnc2n1)N1CCC(N2CCc3ccccc3C2)C(O)C1]

or a pharmaceutically acceptable salt thereof.

In an embodiment of the invention, the compound is,

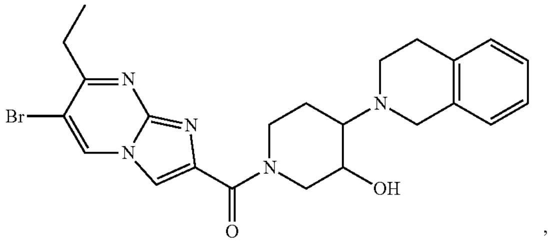 [SMILES: CCc1nc2nc(C(=O)N3CCC(N4CCc5ccccc5C4)C(O)C3)cn2cc1Br]

or a pharmaceutically acceptable salt thereof.

In an embodiment of the invention, the compound is, 1-{4-[(4-{[(3S,4S)-4-(3,4-dihydroisoquinolin-2(1H)-yl)-3-hydroxypiperidin-1-yl]carbonyl}-5-fluoropyridin-2-yl)amino]piperidin-1-yl}ethanone, or a pharmaceutically acceptable salt thereof.

In an embodiment of the invention, the compound is, (6-(2,2-difluorocyclopropyl)imidazo[1,2-a]pyrimidin-2-yl)((3S,4S)-4-(3,4-dihydroisoquinolin-2(1H)-yl)-3-hydroxypiperidin-1-yl)methanone, or a pharmaceutically acceptable salt thereof.

In an embodiment of the invention, the compound is, (6-cyclopropylimidazo[1,2-a]pyrimidin-2-yl)((3S,4S)-4-(3,4-dihydroisoquinolin-2(1H)-yl)-3-hydroxypiperidin-1-yl)methanone, or a pharmaceutically acceptable salt thereof.

In an embodiment of the invention, the compound is, (6-bromo-7-ethylimidazo[1,2-a]pyrimidin-2-yl)((3S,4S)-4-(3,4-dihydroisoquinolin-2(1H)-yl)-3-hydroxypiperidin-1-yl)methanone, or a pharmaceutically acceptable salt thereof.

In one embodiment, the present invention is a composition for treating cancer comprising an effective amount of at least one compound disclosed herein, or a pharmaceutically acceptable salt thereof, and a pharmaceutically acceptable carrier.

The invention also provides a pharmaceutical composition comprising an effective amount of at least one compound disclosed herein, or a pharmaceutically acceptable salt thereof, and an effective amount of at least one other pharmaceutically active ingredient (such as, for example, a chemotherapeutic agent), and a pharmaceutically acceptable carrier.

In one embodiment, the present invention is a composition for treating hemoglobinopathies such as ß-thalassemia or Sickle Cell Disease (SCD), comprising a compound disclosed herein, or a pharmaceutically acceptable salt thereof.

In one embodiment, the present invention is a composition for treating hemoglobinopathies such as ß-thalassemia or Sickle Cell Disease (SCD), comprising a compound disclosed herein, or a pharmaceutically acceptable salt thereof, and a pharmaceutically acceptable carrier.

In one embodiment, the present invention is a method of inhibiting PRMT5 in a patient in need thereof comprising administering to said patient an effective amount of at least one compound disclosed herein, or a pharmaceutically acceptable salt thereof.

In another embodiment, the present invention is a method of treating cancer comprising administering to a patient in need thereof a an effective amount of at least one compound disclosed herein, or a pharmaceutically acceptable salt thereof.

In another embodiment, the present invention provides a method for treating cancer in a patient in need thereof comprising administering to said patient an effective amount of at least one compound disclosed herein, or a pharmaceutically acceptable salt thereof, in combination with an effective amount of at least one chemotherapeutic agent.

The methods of the invention include the administration of a pharmaceutical composition comprising at least one compound disclosed herein and a pharmaceutically acceptable carrier.

In another embodiment, the present invention includes a method of treating hemoglobinopathies such as ß-thalassemia or Sickle Cell Disease (SCD), comprising administering to a patient in need thereof a compound disclosed herein, or a pharmaceutically acceptable salt thereof.

In another embodiment, the present invention is a method of treating cancer comprising administering to a patient in need thereof a compound disclosed herein, or a pharmaceutically acceptable salt thereof.

In another embodiment, the present invention is a method of treating cancer comprising administering to a patient in need thereof a compound disclosed herein, or a pharmaceutically acceptable salt thereof, and a pharmaceutically acceptable carrier.

In another embodiment, the present invention is a method of treating hemoglobinopathies such as ß-thalassemia or Sickle Cell Disease (SCD), comprising administering to a patient in need thereof a compound disclosed herein, or a pharmaceutically acceptable salt thereof.

In another embodiment, the present invention is a method of treating hemoglobinopathies such as ß-thalassemia or Sickle Cell Disease (SCD), comprising administering to a patient in need thereof a compound disclosed herein, or a pharmaceutically acceptable salt thereof, and a pharmaceutically acceptable carrier.

In another embodiment, the present invention is a method of treating cancer comprising administering to a patient in need thereof, a composition comprising a compound disclosed herein, or a pharmaceutically acceptable salt thereof, and a pharmaceutically acceptable carrier.

In another embodiment, the present invention is a method of treating hemoglobinopathies such as ß-thalassemia or Sickle Cell Disease (SCD), comprising administering to a patient in need thereof, a composition comprising a compound disclosed herein, or a pharmaceutically acceptable salt thereof, and a pharmaceutically acceptable carrier.

In another embodiment, the present invention is the use of a compound disclosed herein, or a pharmaceutically acceptable salt thereof, in the manufacture of a medicament for treating cancer.

In another embodiment of the present invention is the use of a compound disclosed herein, or a pharmaceutically acceptable salt thereof, in the manufacture of a medicament for treating hemoglobinopathies such as ß-thalassemia or Sickle Cell Disease (SCD).

In another embodiment, the present invention includes the use of compound disclosed herein, or a pharmaceutically acceptable salt thereof, for the preparation of a medicament for the treatment of cancer, or hemoglobinopathies such as ß-thalassemia or Sickle Cell Disease (SCD).

Another embodiment is the use of compound disclosed herein, or a pharmaceutically acceptable salt thereof, for the preparation of a medicament for the treatment of cancer. In a subembodiment, the cancer is i) cardiac cancer, ii) lung cancer, iii) gastrointestinal cancer, iv) genitourinary tract cancer, v) liver cancer, vi) bone cancer, vii) nervous system cancer, viii) gynecological cancer, ix) hematological cancer, x) skin cancer, or xi) adrenal cancer.

Another embodiment is the use of a compound described herein, or a pharmaceutically acceptable salt thereof, for the preparation of a medicament for the treatment of hemoglobinopathies such as ß-thalassemia or Sickle Cell Disease (SCD).

In another embodiment, the present invention includes compounds disclosed herein, for use in the treatment of cancer or hemoglobinopathies such as ß-thalassemia or Sickle Cell Disease (SCD). In another embodiment, the present invention includes compounds disclosed herein, or a pharmaceutically acceptable salt thereof, for use in the treatment of cardiac cancer, lung cancer, gastrointestinal cancer, genitourinary tract cancer, liver cancer, bone cancer, nervous system cancer, gynecological cancer, hematological cancer, skin cancer, or adrenal cancer.

In one example of the invention the cancer treated is colo-rectal cancer (such as, for example, colon adenocarcinoma and colon adenoma). Thus, another example of the invention is directed to a method of treating colo-rectal cancer in a patient in need of such treatment, said method comprising administering an effective of a compound disclosed herein, or a pharmaceutically acceptable salt thereof, to said patient. Another example of the invention is directed to a method of treating colo-rectal cancer in a patient in need of such treatment, said method comprising administering to said patient an effective amount of a compound disclosed herein, or a pharmaceutically acceptable salt thereof, and an effective amount of at least one chemotherapeutic agent.

The invention also provides any of the above methods of treating cancer wherein the cancer is melanoma. Thus, another example of the invention is directed to a method of treating melanoma in a patient in need of such treatment, said method comprising administering an effective amount of a compound disclosed herein, or a pharmaceutically acceptable salt thereof, to said patient. Another example of the invention is directed to a method of treating melanoma in a patient in need of such treatment, said method comprising administering to said patient an effective amount of a compound disclosed herein, or a pharmaceutically acceptable salt thereof, and an effective amount of at least one chemotherapeutic agent.

The methods of treating cancers described herein can optionally include the administration of an effective amount of radiation (i.e., the methods of treating cancers described herein optionally include the administration of radiation therapy).

The methods of treating cancer described herein include methods of treating cancer that comprise administering a therapeutically effective amount of a compound of the instant invention, or a pharmaceutically acceptable salt thereof, in combination with radiation therapy and/or in combination with a second compound selected from: an estrogen receptor modulator, an androgen receptor modulator, a retinoid receptor modulator, a cytotoxicytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed herein, or a pharmaceutically acceptable salt thereof.

In any of the methods of treating cancer described herein, unless stated otherwise, the methods can optionally include the administration of an effective amount of radiation therapy. For radiation therapy, γ-radiation is preferred.

In one embodiment, the compound disclosed herein is selected from the group consisting of the compounds exemplified herein, for example, in Examples 1-4, or a pharmaceutically acceptable salt thereof.

The term "composition" is intended to encompass a product comprising the specified ingredients in the specified amounts, as well as any product which results, directly or indirectly, from combination of the specified ingredients in the specified amounts. The term "anti-cancer agent" means a drug (medicament or pharmaceutically active ingredient), or antibody for treating cancer. The term "at least one" means one or more than one. The meaning of "at least one" with reference to the number of compounds of the invention is independent of the meaning with reference to the number of chemotherapeutic agents. The term "chemotherapeutic agent" means a drug (medicament or pharmaceutically active ingredient) for treating cancer (i.e., an antineoplastic agent). The term "effective amount" means a "therapeutically effective amount". The term "therapeutically effective amount" means that amount of active compound or pharmaceutical agent that elicits the biological or medicinal response in a tissue, system, animal or human that is being sought by a researcher, veterinarian, medical doctor or other clinician. Thus, for example, in the methods of treating cancer described herein "effective amount" (or "therapeutically effective amount") means, the amount of the compound (or drug), or radiation, that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor. Also, for example, an effective amount, or a therapeutically effective amount of the PRMT5 inhibitor (i.e., a compound of the invention) is that amount which results in the reduction in PRMT5 activity. The term "treating cancer" or "treatment of cancer" refers to administration to a mammal afflicted with a cancerous condition and refers to an effect that alleviates the cancerous condition by killing the cancerous cells, and also refers to an effect that results in the inhibition of growth and/or metastasis of the cancer.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., the Physicians' Desk Reference, $64^{th}$ Edition, 2010 (published by PDR Network, LLC at Montvale, NJ 07645-1725), presently accessible through www.pdr.net; the disclosures of which are incorporated herein by reference thereto.

If the patient is responding, or is stable, after completion of the therapy cycle, the therapy cycle can be repeated according to the judgment of the skilled clinician. Upon completion of the therapy cycles, the patient can be continued on the compounds of the invention at the same dose that was administered in the treatment protocol. This maintenance dose can be continued until the patient progresses or can no longer tolerate the dose (in which case the dose can be reduced and the patient can be continued on the reduced dose).

Those skilled in the art will recognize that the actual dosages and protocols for administration employed in the methods of the invention may be varied according to the judgment of the skilled clinician. The actual dosage employed may be varied depending upon the requirements of the patient and the severity of the condition being treated. Determination of the proper dosage for a particular situation is within the skill of the art. A determination to vary the dosages and protocols for administration may be made after the skilled clinician takes into account such factors as the patient's age, condition and size, as well as the severity of the cancer being treated and the response of the patient to the treatment.

The amount and frequency of administration of the compound disclosed herein and the chemotherapeutic agents will be regulated according to the judgment of the attending clinician (physician) considering such factors as age, condition and size of the patient as well as severity of the cancer being treated.

The compounds of the invention are also useful in preparing a medicament that is useful in treating cancer.

The instant compounds are also useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in *Cancer Principles and Practice of Oncology* by VT. Devita and S. Hellman (editors), $9^{th}$ edition (May 16, 2011), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, programmed cell death protein 1 (PD-1) inhibitors, programmed death-ligand 1 (PD-L1) inhibitors, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The instant compounds are particularly useful when co-administered with radiation therapy.

The chemotherapeutic agent can be administered according to therapeutic protocols well known in the art. It will be apparent to those skilled in the art that the administration of the chemotherapeutic agent can be varied depending on the cancer being treated and the known effects of the chemotherapeutic agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the cancer to the administered therapeutic agents.

The initial administration can be made according to established protocols known in the art, and then, based upon the observed effects, the dosage, modes of administration and times of administration can be modified by the skilled clinician.

The particular choice of chemotherapeutic agent will depend upon the diagnosis of the attending physicians and their judgement of the condition of the patient and the appropriate treatment protocol.

The determination of the order of administration, and the number of repetitions of administration of the chemotherapeutic agent during a treatment protocol, is well within the knowledge of the skilled physician after evaluation of the cancer being treated and the condition of the patient.

Thus, in accordance with experience and knowledge, the practicing physician can modify each protocol for the administration of a chemotherapeutic agent according to the individual patient's needs, as the treatment proceeds. All such modifications are within the scope of the present invention.

The anti-cancer agent can be administered according to therapeutic protocols well known in the art. It will be apparent to those skilled in the art that the administration of the anti-cancer agent can be varied depending on the cancer being treated and the known effects of the anti-cancer agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the cancer to the administered therapeutic agents.

The initial administration can be made according to established protocols known in the art, and then, based upon the observed effects, the dosage, modes of administration and times of administration can be modified by the skilled clinician.

The particular choice of anti-cancer agent will depend upon the diagnosis of the attending physicians and their judgement of the condition of the patient and the appropriate treatment protocol.

The determination of the order of administration, and the number of repetitions of administration of the anti-cancer agent during a treatment protocol, is well within the knowledge of the skilled physician after evaluation of the cancer being treated and the condition of the patient.

Thus, in accordance with experience and knowledge, the practicing physician can modify each protocol for the administration of an anti-cancer agent according to the individual patient's needs, as the treatment proceeds. All such modifications are within the scope of the present invention.

The attending clinician, in judging whether treatment is effective at the dosage administered, will consider the general well-being of the patient as well as more definite signs such as relief of cancer-related symptoms (e.g., pain), inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

The compounds, compositions and methods provided herein are useful for the treatment of cancer. Cancers that may be treated by the compounds, compositions and methods disclosed herein include, but are not limited to: (1) Cardiac: sarcoma (angiosarcoma, fibrosarcoma, rhabdomyosarcoma, liposarcoma), myxoma, rhabdomyoma, fibroma, lipoma and teratoma; (2) Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma, non-small cell; (3) Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; (4) Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); (5) Liver: hepatoma (hepatocellular carcinoma), cholangiocarcinoma, hepatoblastoma, angiosarcoma, hepatocellular adenoma, hemangioma; (6) Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; (7) Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); (8) Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; (9) Hematologic: blood (myeloid leukemia [acute and chronic], acute lymphoblastic leukemia, chronic lymphocytic leukemia, chronic myelomonocytic (CMML), myeloproliferative diseases, multiple myeloma, myelodysplastic syndrome), Hodgkin's disease, non-Hodgkin's lymphoma [malignant lymphoma]; (10) Skin: malignant melanoma, basal cell carcinoma, squamous cell carcinoma, Karposi's sarcoma, moles dysplastic nevi, lipoma, angioma, dermatofibroma, keloids, psoriasis; and (11) Adrenal glands: neuroblastoma. Examples of cancer that may be treated by the compounds, compositions and methods of the invention include thyroid cancer, anaplastic thyroid carcinoma, epidermal cancer, head and neck cancer (e.g., squamous cell cancer of the head and neck), sarcoma, tetracarcinoma, hepatoma and multiple myeloma. Thus, the term "cancerous cell" as provided herein, includes a cell afflicted by any one of the above-identified conditions.

In the treatment of breast cancer (e.g., postmenopausal and premenopausal breast cancer, e.g., hormone-dependent breast cancer) the compounds disclosed herein may be used with an effective amount of at least one antihormonal agent selected from the group consisting of: (a) aromatase inhibitors, (b) antiestrogens, and (c) LHRH analogues; and optionally an effective amount of at least one chemotherapeutic agent. Examples of aromatase inhibitors include but are not limited to: Anastrozole (e.g., Arimidex), Letrozole (e.g., Femara), Exemestane (Aromasin), Fadrozole and Formestane (e.g., Lentaron). Examples of antiestrogens include but are not limited to: Tamoxifen (e.g., Nolvadex), Fulvestrant (e.g., Faslodex), Raloxifene (e.g., Evista), and Acolbifene. Examples of LHRH analogues include but are not limited to: Goserelin (e.g., Zoladex) and Leuprolide (e.g., Leuprolide Acetate, such as Lupron or Lupron Depot). Examples of chemotherapeutic agents include but are not limited to: Trastuzumab (e.g., Herceptin), Gefitinib (e.g., Iressa), Erlotinib (e.g., Erlotinib HCl, such as Tarceva), Bevacizumab (e.g., Avastin), Cetuximab (e.g., Erbitux), and Bortezomib (e.g., Velcade).

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

PD-1 inhibitors include pembrolizumab (lambrolizumab), nivolumab and MPDL3280A. PDL-inhibitors include atezolizumab, avelumab, and durvalumab.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refers to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, 4-demethoxy-3-deamino-3-aziridinyl-4-methylsulphonyl-daunorubicin (see WO 00/50032), Raf kinase inhibitors (such as Bay43-9006) and mTOR inhibitors (such as Wyeth's CCI-779).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, TDX258, the epothilones (see for example U.S. Pat. Nos. 6,284,781 and 6,288,237) and BMS188797. In an example the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino]ethyl]-5-[4-hydro0xy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoguinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an example inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. J. Med. Chem. 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680 (tozasertib).

"Antiproliferative agents" include antisense RNA and DNA oligonucleotides such as G3139, ODN698, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl) sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitor" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952), rosuvastatin (CRESTOR® U.S. Reissue Patent RE37,314) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefore the use of such salts, esters, open-acid and lactone forms is included within the scope of the invention.

"Prenyl-protein transferase inhibitor" refers to a compound which inhibits any one or any combination of the prenyl-protein transferase enzymes, including famesyl-protein transferase (FPTase), geranylgeranyl-protein transferase type I (GGPTase-I), and geranylgeranyl-protein transferase type-II (GGPTase-II, also called Rab GGPTase). For an example of the role of a prenyl-protein transferase inhibitor on angiogenesis see *European J. of Cancer*, Vol. 35, No. 9, pp.1394-1401 (1999).

"Angiogenesis inhibitor" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (*PNAS*, Vol. 89, p. 7384 (1992); JNCI, Vol. 69, p. 475 (1982); *Arch. Opthalmol.*, Vol. 108, p.573 (1990); *Anat. Rec.*, Vol. 238, p. 68 (1994); *FEBS Letters*, Vol. 372, p. 83 (1995); *Clin, Orthop*. Vol. 313, p. 76 (1995); *J Mol. Endocrinol.*, Vol. 16, p.107 (1996); *Jpn. J Pharmacol.*, Vol. 75, p. 105 (1997); *Cancer Res.*, Vol. 57, p. 1625 (1997); Cell, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature*, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem.* La. Med. 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101: 329-354 (2001)). TAFIa inhibitors have been described in U.S. Ser. Nos. 60/310,927 (filed Aug. 8, 2001) and 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK1 and CHK2 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, *Nature,* 411:355-365, 2001.

"Inhibitors of cell proliferation and survival signalling pathway" refers to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004/0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, U.S. Pat. Nos. 7,454,431, 7,589,068), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

As described above, the combinations with NSAIDs are directed to the use of NSAIDs which are potent COX-2 inhibiting agents. For purposes of the specification an NSAID is potent if it possesses an $IC_{50}$ for the inhibition of COX-2 of 1 μM or less as measured by cell or microsomal assays.

The invention also encompasses combinations with NSAIDs which are selective COX-2 inhibitors. For purposes of the specification NSAIDs which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. Nos. 5,474,995, 5,861,419, 6,001,843, 6,020,343, 5,409,944, 5,436,265, 5,536,752, 5,550,142, 5,604,260, 5,698,584, 5,710,140, WO 94/15932, U.S. Pat. Nos. 5,344,991, 5,134,142, 5,380,738, 5,393,790, 5,466,823, 5,633,272 and 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)-phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: rofecoxib, etoricoxib, parecoxib, BEXTRA® and CELEBREX® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide,CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416), or a pharmaceutically acceptable salt thereof.

As used above, "integrin blockers" refers to compounds which selectively antagonize, inhibit or counteract binding of a physiological ligand to the αvβ3 integrin, to compounds which selectively antagonize, inhibit or counteract binding of a physiological ligand to the αvβ5 integrin, to compounds which antagonize, inhibit or counteract binding of a physiological ligand to both the αvβ3 integrin and the αvβ5 integrin, and to compounds which antagonize, inhibit or counteract the activity of the particular integrin(s) expressed on capillary endothelial cells. The term also refers to antagonists of the αvβ6, αvβ8, α1β1, α2β1, α5β1, α6β1 and α6β4 integrins. The term also refers to antagonists of any combination of αvβ3, αvβ5, αvβ6, αvβ8, α1β1, α2β1, α5β1, α6β1 and α6β4 integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974, or a pharmaceutically acceptable salt thereof.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malignancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913*; J. Biol. Chem.* 1999; 274:9116-9121*; Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice (Arch. Ophthamol. 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, G1262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy) phenoxy)propoxy)-2-ethylchromane-2-carboxylic acid (disclosed in U.S. Ser. No. 60/235,708 and 60/244,697), or a pharmaceutically acceptable salt thereof.

Another example of the instant invention is the use of the presently disclosed compounds in combination with gene therapy for the treatment of cancer. For an overview of genetic strategies to treating cancer see Hall et al., (*Am. J. Hum. Genet.* 61:785-789, 1997) and Kufe et al., (*Cancer Medicine,* 5th Ed, pp 876-889, B C Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar), or a pharmaceutically acceptable salt thereof.

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another example, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

A compound of the instant invention, or a pharmaceutically acceptable salt thereof, may also be administered with an agent useful in the treatment of anemia. Such an anemia treatment agent is, for example, a continuous erythropoiesis receptor activator (such as epoetin alfa).

A compound of the instant invention, or a pharmaceutically acceptable salt thereof, may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention, or a pharmaceutically acceptable salt thereof, may also be administered with an immunologic-enhancing drug, such as levamisole, isoprinosine and Zadaxin, or a pharmaceutically acceptable salt thereof.

A compound of the instant invention, or a pharmaceutically acceptable salt thereof, may also be useful for treating or preventing cancer in combination with P450 inhibitors including: xenobiotics, quinidine, tyramine, ketoconazole, testosterone, quinine, methyrapone, caffeine, phenelzine, doxorubicin, troleandomycin, cyclobenzaprine, erythromycin, cocaine, furafyline, cimetidine, dextromethorphan, ritonavir, indinavir, amprenavir, diltiazem, terfenadine, verapamil, cortisol, itraconazole, mibefradil, nefazodone and nelfinavir, or a pharmaceutically acceptable salt thereof.

A compound of the instant invention, or a pharmaceutically acceptable salt thereof, may also be useful for treating or preventing cancer in combination with Pgp and/or BCRP inhibitors including: cyclosporin A, PSC833, GF120918, cremophorEL, fumitremorgin C, Ko132, Ko134, Iressa, Imatnib mesylate, EKI-785, C11033, novobiocin, diethylstilbestrol, tamoxifen, resperpine, VX-710, tryprostatin A, flavonoids, ritonavir, saquinavir, nelfinavir, omeprazole, quinidine, verapamil, terfenadine, ketoconazole, nifidepine, FK506, amiodarone, XR9576, indinavir, amprenavir, cortisol, testosterone, LY335979, OC144-093, erythromycin, vincristine, digoxin and talinolol, or a pharmaceutically acceptable salt thereof.

A compound of the instant invention, or a pharmaceutically acceptable salt thereof, may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention, or a pharmaceutically acceptable salt thereof, may also be useful for treating or preventing breast cancer in combination with aromatase inhibitors. Examples of aromatase inhibitors include but are not limited to: anastrozole, letrozole and exemestane, or a pharmaceutically acceptable salt thereof.

A compound of the instant invention, or a pharmaceutically acceptable salt thereof, may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139), or a pharmaceutically acceptable salt thereof.

A compound of the instant invention, or a pharmaceutically acceptable salt thereof, may also be useful for treating or preventing cancer in combination with PARP inhibitors.

A compound of the instant invention, or a pharmaceutically acceptable salt thereof, may also be useful for treating cancer in combination with the following therapeutic agents: pembrolizumab (Keytruda®), abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); Ridaforolimus; sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); vorinostat (Zolinza®) and zoledronate (Zometa®), or a pharmaceutically acceptable salt thereof.

In an example, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an example, the estrogen receptor modulator is tamoxifen or raloxifene, or a pharmaceutically acceptable salt thereof.

Thus, the scope of the instant invention encompasses the use of the instantly claimed compounds in combination with a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

Also included in the scope of the claims is a method of treating cancer that comprises administering a therapeutically effective amount of a compound of the instant invention, or a pharmaceutically acceptable salt thereof, in combination with radiation therapy and/or in combination with a second compound selected from: an estrogen receptor modulator, an androgen receptor modulator, a retinoid receptor modulator, a cytotoxiccytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

And yet another example of the invention is a method of treating cancer that comprises administering a therapeutically effective amount of a compound of the instant invention, or a pharmaceutically acceptable salt thereof, in combination with paclitaxel or trastuzumab.

The invention further encompasses a method of treating or preventing cancer that comprises administering a therapeutically effective amount of a compound of the instant invention, or a pharmaceutically acceptable salt thereof, in combination with a COX-2 inhibitor, or a pharmaceutically acceptable salt thereof.

The therapeutic combination disclosed herein may be used in combination with one or more other active agents, including but not limited to, other anti-cancer agents that are used in the prevention, treatment, control, amelioration, or reduction of risk of a particular disease or condition (e.g., cell-proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, prior to, contemporaneously, or sequentially with a compound of the present disclosure.

The instant invention also includes a pharmaceutical composition useful for treating or preventing cancer that comprises a therapeutically effective amount of a compound of the instant invention, or a pharmaceutically acceptable salt thereof, and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

The present invention includes compounds disclosed herein, as well as the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of the invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, 4-bromobenzenesulfonate, butyrate, camphorate, camphorsulfonate, camsylate, carbonate, chloride, clavulanate, citrate, cyclohexylamidosulfonate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glucuonate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, trifluoromethylsulfonate, p-toluenesulfonate, undeconate, valerate and the like.

Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts.

With basic reagents such as hydroxides, carbonates, hydrogencarbonates, alkoxides and ammonia, organic bases or alternatively basic amino acids the compounds disclosed herein form stable alkali metal, alkaline earth metal or optionally substituted ammonium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethanolamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, ornithine, piperazine, piperidine, polyamine resins, procaine, purines, theobromine, triethanolamine, triethylamine, trimethylamine, tripropylamine, trometamol, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The preparation of pharmacologically acceptable salts from compounds disclosed herein capable of salt formation, including their stereoisomeric forms is carried out known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

The present invention encompasses all stereoisomeric forms of the compounds disclosed herein. When bonds to the chiral carbon are depicted as straight lines in the structural Formulas of the invention, it is understood that both the (R) and (S) configurations of the chiral carbon, and hence both enantiomers and mixtures thereof, are embraced within the compounds. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of the invention.

Absolute stereochemistry may be determined by X-ray crystallography of crystalline products or crystalline intermediates which are derivatized, if necessary, with a reagent containing a stereogenic center of known configuration. Where compounds of the invention are capable of tautomerization, all individual tautomers as well as mixtures thereof are included in the scope of the invention. The present invention includes all such isomers, as well as salts, solvates (including hydrates) and solvated salts of such isomers and tautomers and mixtures thereof.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

Furthermore, compounds of the present invention may exist in amorphous form and/or one or more crystalline forms, and as such all amorphous and crystalline forms and mixtures thereof of the compounds disclosed herein are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of the invention, along with unsolvated and anhydrous forms.

The present invention includes compounds disclosed herein as well as salts thereof, particularly pharmaceutically acceptable salts, solvates of such compounds and solvated salt forms thereof, where such forms are possible unless specified otherwise.

Commonly used abbreviations for alkyl groups are used throughout the specification, e.g. methyl may be represented by conventional abbreviations including "Me" or $CH_3$ or a symbol that is an extended bond as the terminal group, e.g. , ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_1$-$C_4$ alkyl") for example, means linear or branched chain alkyl groups, including all isomers, having the specified number of carbon atoms. For example, the structures

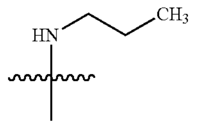

and

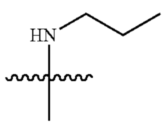

have equivalent meanings. $C_{1-4}$ alkyl includes n-, iso-, sec- and t-butyl, n- and isopropyl, ethyl and methyl. If no number is specified, 1-4 carbon atoms are intended for linear or branched alkyl groups.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

If the compounds disclosed herein simultaneously contain acidic and basic groups in the molecule the invention also includes, in addition to the salt forms mentioned, inner salts or betaines (zwitterions). Salts can be obtained from the compounds disclosed herein by customary methods which are known to the person skilled in the art, for example by combination with an organic or inorganic acid or base in a solvent or dispersant, or by anion exchange or cation exchange from other salts. The present invention also includes all salts of the compounds disclosed herein which, owing to low physiological compatibility, are not directly suitable for use in pharmaceuticals but which can be used, for example, as intermediates for chemical reactions or for the preparation of physiologically acceptable salts.

The invention also includes derivatives of the compounds disclosed herein, acting as prodrugs and solvates. Any pharmaceutically acceptable pro-drug modification of a compound of the invention which results in conversion in vivo to a compound within the scope of the invention is also within the scope of the invention. Prodrugs, following administration to the patient, are converted in the body by normal metabolic or chemical processes, such as through hydrolysis in the blood, to the compounds disclosed herein. Such prodrugs include those that demonstrate enhanced bioavailability, tissue specificity, and/or cellular delivery, to improve drug absorption of the compounds disclosed herein. The effect of such prodrugs may result from modification of physicochemical properties such as lipophilicity, molecular weight, charge, and other physicochemical properties that determine the permeation properties of the drug. For example, esters can optionally be made by esterification of an available carboxylic acid group or by formation of an ester on an available hydroxy group in a compound. Similarly, labile amides can be made. Pharmaceutically acceptable esters or amides of the compounds of the invention may be prepared to act as pro-drugs which can be hydrolyzed back to an acid (or —COO— depending on the pH of the fluid or tissue where conversion takes place) or hydroxy form particularly in vivo and as such are encompassed within the scope of the invention. Examples of pharmaceutically acceptable pro-drug modifications include, but are not limited to, —$C_{1-6}$alkyl esters and —$C_{1-6}$alkyl substituted with phenyl esters.

When any variable occurs more than one time in any constituent or in the schemes disclosed herein, its definition on each occurrence is independent of its definition at every other occurrence. Also, combinations of substituents and/or variables are permissible only if such combinations result in stable compounds.

Except where noted, the term "halogen" means fluorine, chlorine, bromine or iodine.

Where ring atoms are represented by variables such as "X", e.g,

the variables are defined by indicating the atom located at the variable ring position without depicting the ring bonds associated with the atom. For example, when X in the above ring is nitrogen, the definition will show "N" and will not depict the bonds associated with it, e.g., will not show "═N—". Likewise, when X is a carbon atom that is substituted with bromide, the definition will show "C—Br" and will not depict the bonds associated with it, e.g., will not show

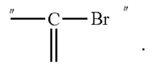

The invention also relates to medicaments containing at least one compound of those disclosed herein and/or of a pharmaceutically acceptable salt of the compound and an optionally stereoisomeric form of the compound or a pharmaceutically acceptable salt of the stereoisomeric form of the compound, together with a pharmaceutically acceptable vehicle, carrier, additive and/or other active substances and auxiliaries.

The medicaments according to the invention can be administered by oral, inhalative, rectal or transdermal administration or by subcutaneous, intraarticular, intraperitoneal or intravenous injection. Oral administration is preferred. Coating of stents with compounds disclosed herein and other surfaces which come into contact with blood in the body is possible.

The invention also relates to a process for the production of a medicament, which comprises bringing at least one compound disclosed herein into a suitable administration form using a pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the compounds, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the compounds may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver about 0.01 mg per kg of body weight per day (mg/kg/day) to about 30 mg/kg/day, preferably 0.025-7.5 mg/kg/day, more preferably 0.1-2.5 mg/kg/day, and even more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

The compounds of the invention may be prepared by employing reactions as shown in the following Reaction Schemes, in addition to other standard manipulations that are known in the literature or exemplified in the experimental procedures. The illustrative Reaction Schemes below, therefore, are not limited by the compounds listed or by any particular substituents employed for illustrative purposes.

Methods for Making the Compounds of Present Invention

General Methods

The compounds of the present invention can be readily produced from known compounds or commercially available compounds by, for example, known processes described in published documents, and produced by production processes described below. The present invention is not limited to the production processes described below. The invention also includes processes for the preparation of compounds of the invention.

It should be noted that, when a compound disclosed herein has a reactive group such as hydroxy group, amino group, carboxyl group, or thiol group as its substituent, such group may be adequately protected with a protective group in each reaction step and the protective group may be removed at an subsequent stage. The process of such introduction and removal of the protective group may be adequately determined depending on the group to be protected and the type of the protective group, and such introduction and removal are conducted, for example, by the process described in the review section of Greene, T. W., et. al., "*Protective Groups in Organic Synthesis*", 2007, 4th Ed., Wiley, New York, or Kocienski, P., "*Protecting Groups*" 1994, Thieme.

It should be noted that, if a discrepancy between the chemical name and structure exists, the structure is understood to dominate.

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claim.

All solvents used were commercially available and were used without further purification. Reactions were typically run using anhydrous solvents under an inert atmosphere of nitrogen.

Starting materials used were either available from commercial sources or prepared according to literature procedures and had experimental data in accordance with those reported.

Abbreviations Used are Those Conventional in the Art of the Following

ACN acetonitrile
Ar Aryl
Aq. Aqueous
BSA bovine serum albumin
Boc tert-Butyloxycarbonyl protecting group
BrettPhos G3 [(2-Di-cyclohexylphosphino-3,6-dimethoxy-2',4',6'-triisopropyl-1,1'-biphenyl)-2-(2'-amino-1,1'-biphenyl)]palladium(II) methanesulfonate methanesulfonate
° C. degree Celsius
$CDCl_3$ deuterated chloroform
$CD_3OD$ deuterated methanol
$CHCl_3$ chloroform
$Cs_2CO_3$ cesium carbonate
DCM dichloromethane
DIEA N,N-diisopropylethylamine
DMA N,N-dimethylacetamide
DMF N,N-dimethylformamide
DMSO dimethylsulfoxide
DTT dithiothreitol
EtOAc ethyl acetate
EtOH ethanol
g gram
h hour(s)
$H_2$ Hydrogen
$H_2O$ Water
HATU N-[(Dimethylamino)-1H-1,2,3-triazolo-[4,5-b]pyridin-1-ylmethylene]-N-methylmethanaminium hexafluorophosphate N-oxide
HCl hydrochloric acid
HPLC High Performance Liquid Chromatography
$K_2CO_3$ potassium carbonate
L Liter
LCMS liquid chromatography and mass spectrometry
LiBr lithium bromide
M molar
MHz Megahertz
MeCN Acetonitrile
MeOH methanol
MS mass spectrometry
MsCl methanesulfonyl chloride
mmol millimole
mg milligram
min minutes
mL milliliter(s)
$N_2$ nitrogen
NaH sodium hydride
$NaHCO_3$Sodium Bicarbonate
NaI sodium iodide
NaOH Sodium Hydroxide
NBS N-bromosuccinimide
nM nanomolar
NMP N-methyl-2-pyrrolidone
N normal
$NH_3$ $H_2O$ ammonia in water
$NH_4OH$ ammonium hydroxide
NMR nuclear magnetic resonance
Pd/C or Pd—C palladium on carbon
$PdCl_2$(dppf) [1,1-bis(diphenylphosphine)ferrocene]dichloropalladium(II)
Pet. Ether Petroleum ether
psi pound per square inch
rt room temperature
sat. saturated
SM starting material
SFC Supercritical fluid chromatography
tBuOK potassium tert-butoxide (or t-BuOK)
T3P propylphosphonic anhydride
TBAB tetrabutylammonium bromide
TEA triethylamine
TFA trifluoroacetic acid
TfOH trifluromethane sulfonic acid
THF tetrahydrofuran
TLC thin layer chromatography
Prep. TLC preparative TLC
$TMSCBrF_2$ (bromodifluoromethyl)trimethylsilane
μL microliter
vol volume General Synthetic Schemes While the present invention has been described in conjunction with the specific examples set forth above, many alternatives, modifications and variations thereof will be apparent to those of ordinary skill in the art. In some cases, the order of carrying out the steps of the reaction schemes may be varied to facilitate the reaction or to avoid unwanted reaction products. All such alternatives, modifications and variations are intended to fall within the spirit and scope of the present invention. Starting materials and intermediates are purchased from commercial sources, made from known procedures, or are otherwise illustrated.

Several methods for preparing the compounds of this invention are described in the following Schemes and Examples. Unless otherwise indicated, all variables are as previously defined. In all general schemes Ar implies an optionally substituted aryl or heteroaryl moiety.

Scheme 1

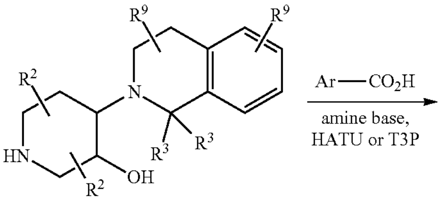

1

-continued

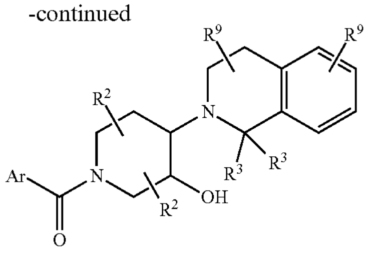

2

In Scheme 1, optionally substituted hydroxypiperidines 1 can be coupled to an optionally substituted aryl or heteroaryl carboxylic acid using standard amide coupling conditions to afford amide 2.

$R^2$ is hydrogen.

$R^3$ is hydrogen.

$R^9$ is hydrogen.

Scheme 2

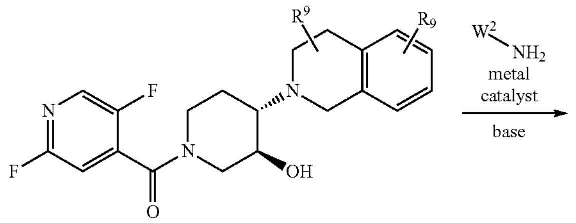

3

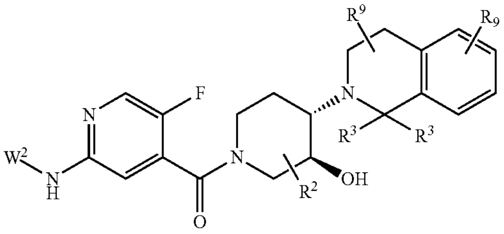

4

In Scheme 2, optionally substituted bromopyridines 3 can be cross-coupled with substituted amines in the presence of a metal catalyst to generate compounds of the form 4.

$W^2$ is

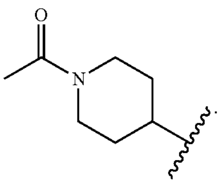 [SMILES: *C1CCN(C(C)=O)CC1]

SYNTHESIS OF INTERMEDIATES

Intermediate 1: (3 S,4S)-4-(3,4-dihydroisoquinolin-2(1H)-yl)piperidin-3-ol

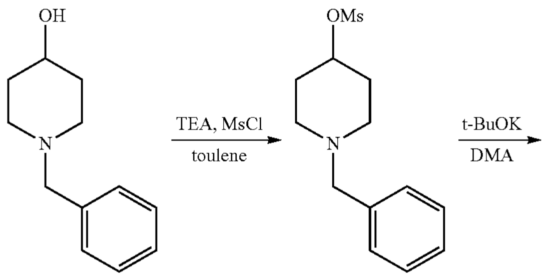

1

2

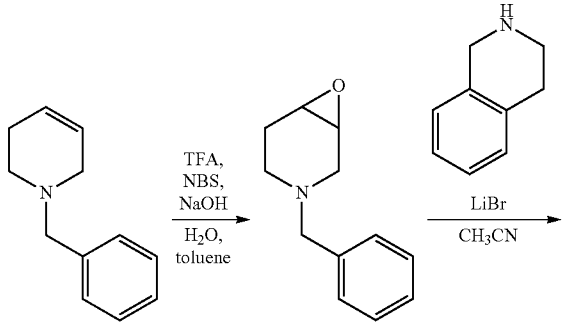

3

4

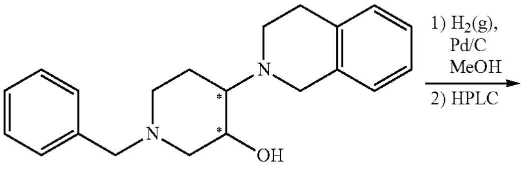

5 - trans

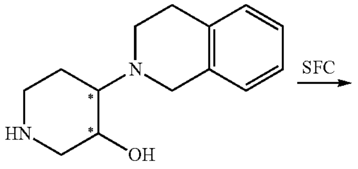

6

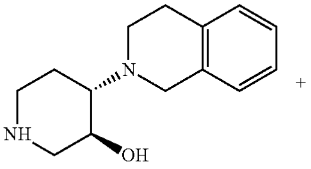

+

Intermediate 1

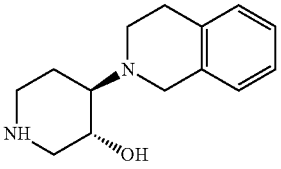

7

Step 1: To a solution of 1-benzylpiperidin-4-ol (200 g, 1.05 mol) in toluene (1.6 L) was added TEA (175 mL, 1.25 mol) dropwise at 25° C. MsCl (97.1 mL, 1.25 mol) was added to the mixture dropwise slowly at 0° C. The mixture was stirred at 25° C. for 2 h. Water (750 mL) was added to the mixture. The organic layer was washed with water (2×400 mL), dried over anhydrous sodium sulfate, filtered, and concentrated under reduced pressure to afford 1-benzylpiperidin yl methanesulfonate, which was used without further purification.

Step 2: To a solution of 1-benzylpiperidin-4-yl methanesulfonate (280 g, 1.04 mol) in DMA (800 mL) was added t-BuOK (175 g, 1.56 mol) portionwise at 25° C. The mixture was stirred at 45° C. for 8 h. The reaction was quenched with water (1.0 L) and the mixture was extracted with EtOAc (600 mL×3). The organic layer was washed with brine (2×500 mL), dried over anhydrous sodium sulfate, filtered, and concentrated under reduced pressure to afford 1-benzyl-1,2,3,6-tetrahydropyridine as a solid. This material was used without further purification. $^1$H NMR (400 MHz, $CDCl_3$) δ 7.28-7.14 (m, 5H), 5.68-5.65 (m, 1H), 5.59-5.55 (m, 1H), 3.50 (s, 2H), 2.91-2.87 (m, 2H), 2.49-2.46 (m, 2H), 2.10-2.06 (m, 2H).

Step 3: To a solution of 1-benzyl-1,2,3,6-tetrahydropyridine (160 g, 924 mmol) in water (1.0 L) was added TFA (68.4 mL, 924 mmol) dropwise at 25° C. To the mixture was added NBS (197 g, 1.11 mol) portionwise slowly at 25° C. The mixture was stirred at 45° C. for 12 h. Toluene (1.2 L) at 25° C. was added to the mixture and then a solution of NaOH (240 g, 6.00 mol) in $H_2O$ (260 mL). The mixture was stirred at 45° C. for 1 h. The aqueous layer was extracted with EtOAc (1.2 L×2) and the combined organic layers were washed with brine (2×1.0 L), dried over anhydrous sodium sulfate, filtered, and concentrated under reduced pressure. The residue was purified by column chromatography on silica (0-15% ethyl acetate/pet. ether gradient) to give 3-benzyl-7-oxa-3-azabicyclo[4.1.0]heptane as an oil, which was used without further purification.

Step 4: To a solution of 3-benzyl-7-oxa-3-azabicyclo[4.1.0]heptane (80 g, 423 mmol) in ACN (600 mL) was added LiBr (66.1 g, 761 mmol) portionwise at 25° C. The mixture was stirred at 30° C. for 0.5 h. To the mixture was added 1,2,3,4-tetrahydroisoquinoline (53.1 mL, 423 mmol) portionwise slowly at 25° C. The mixture was stirred at 30° C. for 10 h. To the mixture was added water (250 mL) and EtOAc (250 mL). The combined organic layers were washed with brine (2×250 L), dried over anhydrous sodium sulfate, filtered, and concentrated under reduced pressure. The residue was purified by column chromatography on silica (60% ethyl acetate/pet. ether gradient) to give trans-1-benzyl-4-(3,4-dihydroisoquinolin-2(1H)-yl)piperidin-3-ol as an oil. $^1$H NMR (400 MHz, $CDCl_3$) δ 7.28-7.21 (m, 5H), 7.10-7.07 (m, 3H), 7.07-6.97 (m, 1H), 3.91-3.87 (m, 1H), 3.72-3.64 (m, 2H), 3.54-3.52 (m, 2H), 3.20-3.15 (m, 1H), 3.03-2.99 (m, 1H), 2.98-2.96 (m, 1H), 2.87-2.84 (m, 2H), 2.61-2.58 (m, 1H), 2.37-2.30 (m, 1H), 1.97-1.96 (m, 1H), 1.89-1.83 (m, 1H), 1.73-1.69 (m, 1H), 1.61-1.55 (m, 1H).

Step 5: A solution of trans-1-benzyl-4-(3,4-dihydroisoquinolin-2(1H)-yl)piperidin-3-ol (90 g, 279 mmol) in MeOH (800 mL) was added to a bottle containing Pd—C(10% wt; 40 g) under a $N_2$ atmosphere. The mixture was degassed and backfilled with H2 (three times). The resultant mixture was stirred under H2 (50 psi) at 50° C. for 6 h. The catalyst was filtered, and the filtrate was concentrated under reduced pressure. The residue was purified by preparative HPLC (water/ACN with 0.05% ammonium hydroxide modifier) to give trans-4-(3,4-dihydroisoquinolin-2(1H)-yl)piperidin-3-ol (Intermediate 1) as an oil, which could be used in subsequent reactions. MS: 233 (M+1).

Trans-4-(3,4-dihydroisoquinolin-2(1H)-yl)piperidin-3-ol was purified by chiral SFC (Chiralpak AD-H column, isopropanol/$CO_2$) to afford two products as solids:

Intermediate 1 (peak 1): (3S,4S)-4-(3,4-dihydroisoquinolin-2(1H)-yl)piperidin-3-ol. $^1$H NMR (400 MHz, DMSO-$d_6$) δ 7.10-7.01 (m, 4H), 4.16 (br s, 1H), 3.85-3.71 (m, 2H), 3.48-3.46 (m, 1H), 3.02-2.91 (m, 1H), 2.89-2.88 (m, 2H), 2.79-2.73 (m, 3H), 2.39-2.35 (m, 2H), 2.22-2.19 (m, 1H), 2.0 (br s, 1H), 1.70-1.65 (m, 1H), 1.37-1.30 (m, 1H)

Peak 2: (3R,4R)-4-(3,4-dihydroisoquinolin-2(1H)-yl)piperidin-3-ol. $^1$H NMR (400 MHz, DMSO-$d_6$) δ 7.15-7.01 (m, 4H), 4.18 (br s, 1H), 3.86-3.72 (m, 2H), 3.49-3.47 (m, 1H), 3.01-2.90 (m, 1H), 2.90-2.89 (m, 2H), 2.80-2.72 (m, 3H), 2.39-2.35 (m, 2H), 2.21-2.20 (m, 1H), 2.0 (br s, 1H), 1.70-1.65 (m, 1H), 1.38-1.31 (m, 1H).

Intermediate 2: 6-(2,2-difluorocyclopropyl)imidazo[1,2-α]pyrimidine-2-carboxylic acid

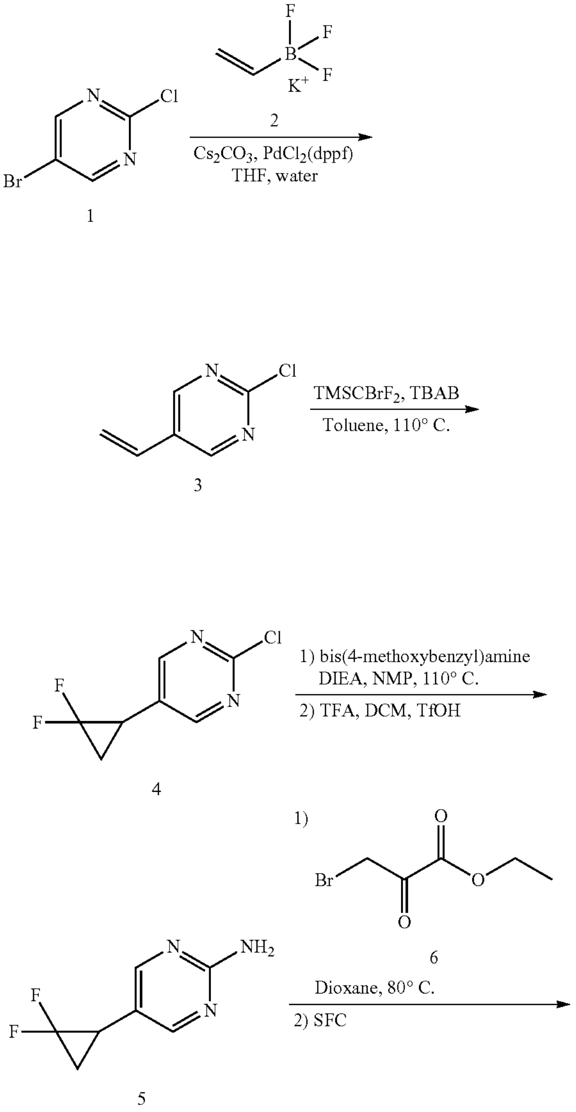

-continued

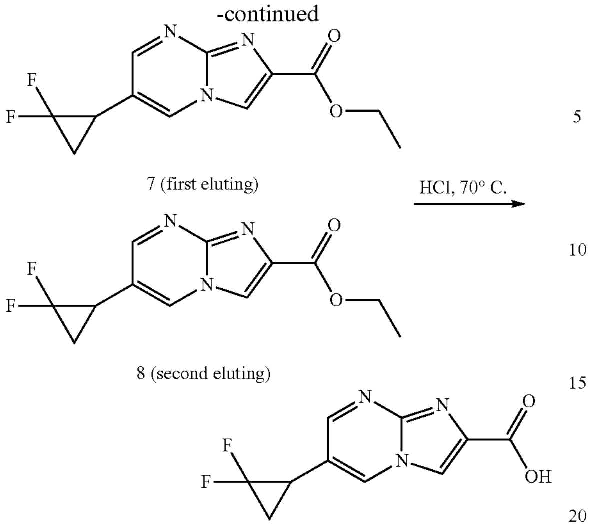

7 (first eluting)

8 (second eluting)

Intermediate 2

Step 1: To a solution of 5-bromo-2-chloropyrimidine (200 mg, 1.03 mmol) in THF (5 mL) and water (1 mL) was added potassium trifluoro(vinyl)borate (230 mg, 1.55 mmol), $Cs_2CO_3$ (1010 mg, 3.10 mmol), and $PdCl_2$(dppf) (151 mg, 0.207 mmol). The reaction mixture was stirred at 85° C. for 2 h under an atmosphere of nitrogen. The reaction was cooled to room temperature and treated with water. The mixture was extracted with EtOAc (3x30 mL), and the combined organic layers were dried over anhydrous sodium sulfate, filtered, and concentrated under reduced pressure. The residue was purified by column chromatography on silica (3% ethyl acetate/pet. ether) to afford 2-chloro-5-vinylpyrimidine as a solid. MS: 141 (M+1).

Step 2: A mixture of tetrabutylammonium bromide (0.193 g, 0.598 mmol), 2-chloro-5-vinylpyrimidine (1.4 g, 10 mmol) and (bromodifluoromethyl)trimethylsilane (6.07 g, 29.9 mmol) in toluene (5 mL) was stirred at 110° C. for 2 h. After cooling to room temperature, the mixture was concentrated under reduced pressure, and the residue was purified by column chromatography on silica (10/1 to 5/1 v/v pet. ether/ethyl acetate) to afford 2-chloro-5-(2,2-difluorocyclopropyl)pyrimidine as a solid. MS: 191 (M+1). $^1$H NMR (400 MHz, $CDCl_3$) δ 8.51 (s, 2H), 2.79-2.60 (m, 1H), 2.08-1.98 (m, 1H), 1.76-1.62 (m, 1H).

Step 3: A mixture of DIEA (9.6 mL, 55 mmol), bis(4-methoxybenzyl)amine (9.5 g, 37 mmol) and 2-chloro-5-(2,2-difluorocyclopropyl)pyrimidine (3.5 g, 18 mmol) in NMP (70 mL) was heated at 110° C. for 12 h. The reaction was cooled to room temperature and diluted with water. The mixture was extracted with EtOAc (3x50 mL). The combined organic layers were dried over anhydrous sodium sulfate, filtered, and concentrated under reduced pressure. The residue was purified by column chromatography on silica (5% ethyl acetate/pet. ether) to afford 5-(2,2-difluorocyclopropyl)-N,N-bis(4-methoxybenzyl)pyrimidin-2-amine as an oil. MS: 412 (M+1).

Step 4: A mixture of 5-(2,2-difluorocyclopropyl)-N,N-bis(4-methoxybenzyl)pyrimidin-2-amine (6.0 g, 15 mmol) in DCM (10 mL), TFA (10 mL), and TfOH (0.1 mL) was stirred at room temperature for 12 h. The mixture was concentrated under reduced pressure, and the residue was dissolved in water (50 mL) and basified with $NH_3H_2O$ to pH ~10. The aqueous layer was extracted with DCM (3x50 mL), and the combined organic layers were washed with brine (50 mL), dried over anhydrous sodium sulfate, filtered, and concentrated under reduced pressure. The residue was purified by column chromatography on silica (100/1 to ⅓, v/v pet. ether/ethyl acetate) to afford 5-(2,2-difluorocyclopropyl)pyrimidin-2-amine as a solid. MS: 172 (M+1).

Step 5: A mixture of 5-(2,2-difluorocyclopropyl)pyrimidin-2-amine (1.5 g, 8.8 mmol) and ethyl 3-bromo-2-oxopropanoate (2.96 g, 11.4 mmol) in dioxane (20 mL) was stirred at 80° C. for 2 h. The mixture was cooled to room temperature and concentrated under reduced pressure. The residue was purified by reverse phase HPLC (ACN/water with 0.1% TFA modifier) to afford ethyl 6-(2,2-difluorocyclopropyl)imidazo[1,2-a]pyrimidine-2-carboxylate. The racemic mixture was purified by chiral SFC (OD column, 20-30% $EtOH/CO_2$) to afford ethyl 6-(2,2-difluorocyclopropyl)imidazo[1,2-a]pyrimidine-2-carboxylate (isomer 1, first eluting) as a solid. MS: 268 (M+1) and ethyl 6-(2,2-difluorocyclopropyl)imidazo[1,2-a]pyrimidine-2-carboxylate (isomer 2, second eluting) as a solid. MS: 268 (M+1).

Step 6: A solution of ethyl 6-(2,2-difluorocyclopropyl)imidazo[1,2-a]pyrimidine-2-carboxylate (isomer 1, first eluting) (180 mg, 0.674 mmol) in HCl (35% in water, 5 mL) was stirred at 70° C. for 12 h. The mixture was cooled to room temperature, concentrated under reduced pressure to afford 6-(2,2-difluorocyclopropyl)imidazo[1,2-a]pyrimidine-2-carboxylic acid as a solid, which was used in the next step without further purification. MS: 240 (M+1). Note that both isomers could be hydrolyzed via the conditions described above.

Intermediate 3: 6-cyclopropylimidazo[1,2-a]pyrimidine-2-carboxylic acid

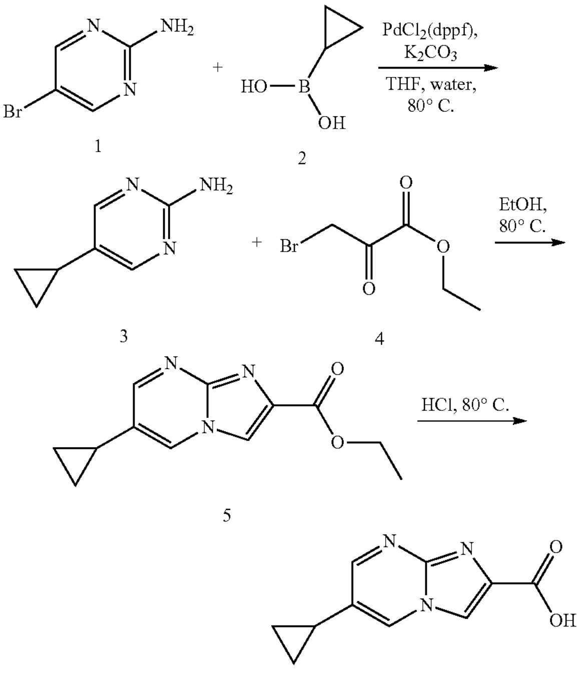

1 2 3 4 5

Intermediate 3

Step 1: To a mixture of 5-bromopyrimidin-2-amine (2.0 g, 12 mmol) in THF (15 mL) and water (3 mL) was added $K_2CO_3$ (4.77 g, 34.5 mmol), cyclopropylboronic acid (4.94 g, 57.5 mmol), and $PdCl_2$(dppf) (0.841 g, 1.15 mmol). The mixture was degassed and backfilled with $N_2$ (3×), and the reaction was stirred at 80° C. for 12 h. The mixture was cooled to room temperature and concentrated under reduced pressure. The residue was purified by column chromatography on silica (0-45% ethyl acetate/pet. ether) to afford 5-cyclopropylpyrimidin-2-amine as a solid. MS: 136 (M+1).

Step 2: To a mixture of 5-cyclopropylpyrimidin-2-amine (3.5 g, 26 mmol) in EtOH (50 mL) was added ethyl 3-bromo-2-oxopropanoate (6.1 g, 31 mmol). The mixture was stirred at 80° C. for 16 h. The reaction was cooled to room temperature, and TEA (7.2 mL, 52 mmol) was added. The mixture was stirred at room temperature for 0.5 h. The mixture was concentrated under reduced pressure, and the residue was purified by column chromatography on silica (60% ethyl acetate/pet. ether) to afford ethyl 6-cyclopropylimidazo[1,2-a]pyrimidine-2-carboxylate as a solid. MS: 232 (M+1). $^1H$ NMR (500 MHz, $CDCl_3$) δ 8.50 (d, J=2.4 Hz, 1H), 8.16 (d, J=2.0 Hz, 1H), 8.04 (s, 1H), 4.44 (q, J=7.2 Hz, 2H), 2.03-1.87 (m, 1H), 1.42 (t, J=7.2 Hz, 3H), 1.12-1.04 (m, 2H), 0.80-0.72 (m, 2H).

Step 3: A mixture of ethyl 6-cyclopropylimidazo[1,2-a]pyrimidine-2-carboxylate (100 mg, 0.432 mmol) in HCl (4 M in dioxane, 2 mL) was stirred at 80° C. for 3 h. The reaction was cooled to room temperature, and concentrated under reduced pressure to afford 6-cyclopropylimidazo[1,2-a]pyrimidine-2-carboxylic acid as a solid, which was used in next step without purification. MS: 204 (M+1).

Intermediate 4: 6-bromo-7-ethylimidazo[1,2-a]pyrimidine-2-carboxylic acid

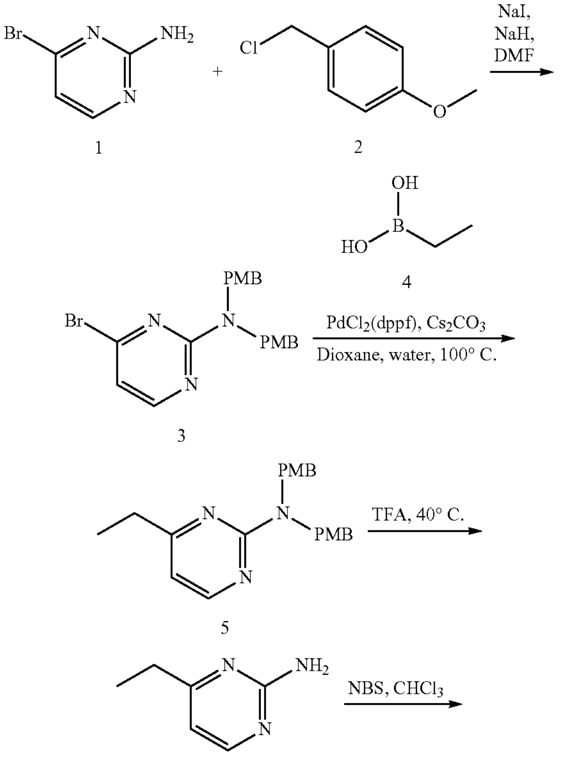

1 2 4 3 5 6

-continued

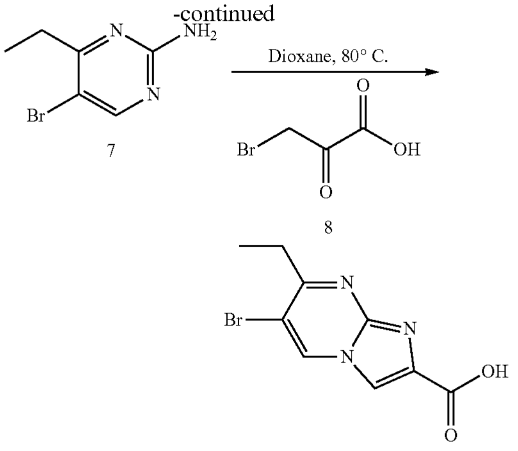

7 8

Intermediate 4

Step 1: To a mixture of 4-bromopyrimidin-2-amine (1 g, 5.8 mmol) and sodium iodide (0.086 g, 0.58 mmol) in DMF (20 mL) was added NaH (0.575 g, 14.4 mmol) at 0° C. The mixture was stirred at 0° C. for 0.5 h, and then 1-(chloromethyl)-4-methoxybenzene (1.98 g, 12.6 mmol) was added. The reaction was stirred at room temperature for 30 min. The mixture was quenched with saturated aqueous ammonium chloride solution (100 mL) and extracted with EtOAc (100 mL). The organic layer was dried over anhydrous sodium sulfate, filtered, and concentrated under reduced pressure. The residue was purified by column chromatography on silica (10% ethyl acetate/pet. ether) to afford 4-bromo-N,N-bis(4-methoxybenzyl)pyrimidin-2-amine as an oil. MS: 414 and 416 (M+1).

Step 2: A mixture of 4-bromo-N,N-bis(4-methoxybenzyl)pyrimidin-2-amine (2 g, 4.8 mmol), ethylboronic acid (1.07 g, 14.5 mmol), PdCl$_2$(dppf) (0.71 g, 0.96 mmol), and $Cs_2CO_3$ (3.15 g, 9.65 mmol) in 1,4-dioxane (10 mL) and water (10 mL) was stirred at 100° C. under an atmosphere of $N_2$ for 10 h. The mixture was cooled to room temperature and concentrated under reduced pressure. The residue was purified by column chromatography on silica (10% ethyl acetate/pet. ether) to afford 4-ethyl-N,N-bis(4-methoxybenzyl)pyrimidin-2-amine as an oil. MS: 364 (M+1). $^1H$ NMR (500 MHz, $CDCl_3$) δ 8.29 (d, J=5.04 Hz, 1H), 7.30-7.24 (m, 4H), 6.94-6.89 (m, 4H), 6.48 (d, J=5.04 Hz, 1H), 4.86 (s, 4H), 3.90-3.84 (m, 6H), 2.77-2.63 (m, 2H), 1.33 (t, J=7.63 Hz, 3H).

Step 3: A mixture of 4-ethyl-N,N-bis(4-methoxybenzyl)pyrimidin-2-amine (900 mg, 2.48 mmol) in TFA (5 mL) was stirred at 40° C. for 12 h. The mixture was cooled to room temperature and quenched with $NH_3.H_2O$ to ~pH 7. The mixture was concentrated under reduced pressure, and the residue was purified by column chromatography on silica (30-60% ethyl acetate/pet. ether) to afford 4-ethylpyrimidin-2-amine as a solid. MS: 124 (M+1). $^1H$ NMR (400 MHz, $CDCl_3$) δ 8.17 (d, J=4.82 Hz, 1H), 6.50 (d, J=5.26 Hz, 1H), 5.04 (br s, 2H), 2.59 (q, J=7.75 Hz, 2H), 1.24 (t, J=7.67 Hz, 3H).

Step 4: To a solution of 4-ethylpyrimidin-2-amine (200 mg, 1.62 mmol) in chloroform (4 mL) was added NBS (318 mg, 1.79 mmol). The mixture was stirred at room temperature for 1 h. The mixture was concentrated under reduced pressure, and the residue was purified by column chromatography on silica (10-80% ethyl acetate/pet. ether) to afford 5-bromo-4-ethylpyrimidin-2-amine as a solid. MS: 202 and 204

(M+1). $^1$H NMR (400 MHz, $CDCl_3$) δ 8.22 (s, 1H), 5.00 (br s, 2H), 2.74 (q, J=7.45 Hz, 2H), 1.23 (t, J=7.67 Hz, 3H).

Step 5: To a solution of 5-bromo-4-ethylpyrimidin-2-amine (100 mg, 0.495 mmol) in 1,4-dioxane (3 mL) was added 3-bromo-2-oxopropanoic acid (99 mg, 0.59 mmol). The reaction was stirred at 80° C. for 15 min. The mixture was cooled to room temperature and concentrated under reduced pressure. The residue was purified by reverse phase HPLC (ACN/water with 0.10% TFA modifier) to afford 6-bromo-7-ethylimidazo[1,2-a]pyrimidine-2-carboxylic acid as a solid. LCSM: 270 and 272 (M+1).

Intermediate 5: (2-bromo-5-fluoropyridin-4-yl)((3S,4S)-4-(3,4-dihydroisoquinolin-2(1H)-yl)-3-hydroypiperidin-1-yl)methanone

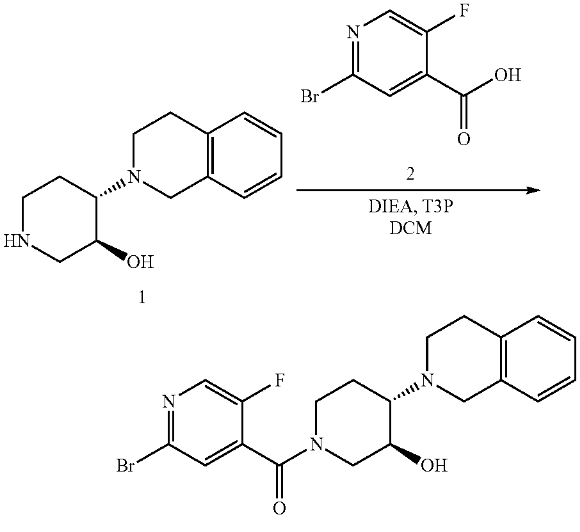

1

Intermediate 5

To a solution of 2-bromo-5-fluoroisonicotinic acid (538 mg, 2.44 mmol) and (3S,4S)-4-(3,4-dihydroisoquinolin-2(1H)-yl)piperidin-3-ol (568 mg, 2.44 mmol) in DCM (11 mL) and DMF (5 mL) at 0° C. was added DIEA (1.7 mL, 9.8 mmol) and T3P (1.7 mL, 2.9 mmol, 50% in DMF). The mixture was stirred at room temperature for 1 h. The reaction was quenched with saturated aqueous $NaHCO_3$(25 mL), and extracted with EtOAc (50 mL×2). The combined organic layers were washed with brine, dried over anhydrous sodium sulfate, filtered, and concentrated under reduced pressure. The residue was purified by column chromatography on silica (0-60% 3:1 EtOAc:EtOH in hexanes) to give (2-bromo-5-fluoropyridin-4-yl)((3S,4S)-4-(3,4-dihydroisoquinolin-2(1H)-yl)-3-hydroxypiperidin-1-yl)methanone. MS: 434 and 436 (M+1).

EXAMPLES

The following experimental procedures detail the preparation of specific examples of the instant disclosure.

Note: Many of the compounds claimed exist as a mixture of rotamers in solution at room temperature, which complicates their analyses by 1H-NMR spectroscopy. In these cases, the peak shifts are listed as ranges of multiplets that encompass the signals from both rotamers, rather than describing individual rotamer peaks.

Example 1: 1-{4-[(4-{[(3S,4S)-4-(3,4-dihydroisoquinolin-2(1H)-yl)-3-hydroxypiperidin-1-yl]carbonyl}-5-fluoropyridin-2-yl)amino]piperidin-1-yl}ethanone

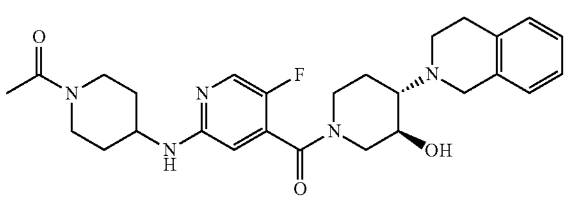 [SMILES: CC(=O)N1CCC(Nc2cc(C(=O)N3CC[C@H](N4CCc5ccccc5C4)[C@@H](O)C3)c(F)cn2)CC1]

A vial under an argon atmosphere was charged with (2-bromo-5-fluoropyridin-4-yl)((3S,4S)-4-(3,4-dihydroisoquinolin-2(1H)-yl)-3-hydroxypiperidin-1-yl)methanone (300 mg, 0.691 mmol), 1-(4-aminopiperidin-1-yl)ethanone (98 mg, 0.69 mmol), $Cs_2CO_3$ (675 mg, 2.07 mmol), and THF (4.6 mL). The mixture was purged with argon for 10 min. Brett Phos precat G3 (63 mg, 0.069 mmol) was added and the mixture was further purged with argon for 10 min. The reaction was stirred at 45° C. for 18 h. The mixture was filtered, diluted with water, and the aqueous layer was extracted with EtOAc (2×). The combined organic layers were dried over anhydrous sodium sulfate, filtered, and concentrated under reduced pressure. The residue was purified by column chromatography on silica (0-100% 3:1 EtOAc:EtOH in hexanes) to give 1-{4-[(4-{[(3S,4S)-4-(3,4-dihydroisoquinolin-2(1H)-yl)-3-hydroxypiperidin-1-yl]carbonyl}-5-fluoropyridin-2-yl)amino]piperidin-1-yl}ethanone as a solid. MS: 496 (M+1). $^1$H NMR (600 MHz, $CD_3OD$) δ 7.97 (d, J=10.4 Hz, 1H), 7.13-7.08 (m, 3H), 7.08-7.03 (m, 1H), 6.48 (d, J=10.0 Hz, 1H), 4.78-4.73 (m, 1H), 4.67-4.58 (m, 1H), 4.44-4.38 (m, 1H), 4.01-3.85 (m, 4H), 3.83-3.76 (m, 1H), 3.75-3.70 (m, 1H), 3.66-3.61 (m, 1H), 3.22-3.15 (m, 1H), 3.07-2.99 (m, 2H), 2.96-2.88 (m, 4H), 2.82-2.74 (m, 2H), 2.13 (s, 3H), 2.08-2.00 (m, 2H), 1.96-1.90 (m, 1H), 1.71-1.54 (m, 1H), 1.51-1.34 (m, 2H).

TABLE 1

The following compounds are the deuterated versions of the above compound.

| | | | |
|---|---|---|---|
| 1b | 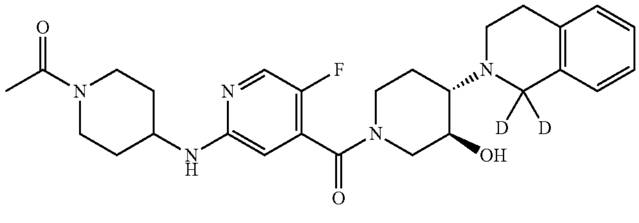 | 1-(4-((4-((3S,4S)-4-(3,4-dihydroisoquinolin-2(1H)-yl-1,1-d2)-3-hydroxypiperidine-1-carbonyl)-5-fluoropyridin-2-yl)amino)piperidin-1-yl)ethan-1-one | 498 |

TABLE 1-continued

| The following compounds are the deuterated versions of the above compound. | | | |
|---|---|---|---|
| 1c | 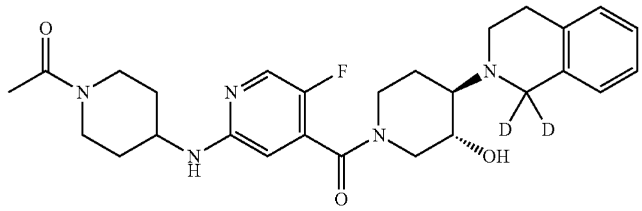 [SMILES: [2H]C1([2H])c2ccccc2CCN1[C@@H]1CCN(C(=O)c2cc(NC3CCN(C(C)=O)CC3)ncc2F)C[C@H]1O] | 1-(4-((4-((3R,4R)-4-(3,4-dihydroisoquinolin-2(1H)-yl-1,1-d2)-3-hydroxypiperidine-1-carbonyl)-5-fluoropyridin-2-yl)amino)piperidin-1-yl)ethan-1-one | 498 |

Example 2: (6-(2,2-difluorocyclopropyl)imidazo[1,2-a]pyrimidin-2-yl)((3S,4S)-4-(3,4-dihydroisoquinolin-2(1H)-yl)-3-hydroxypiperidin-1-yl)methanone

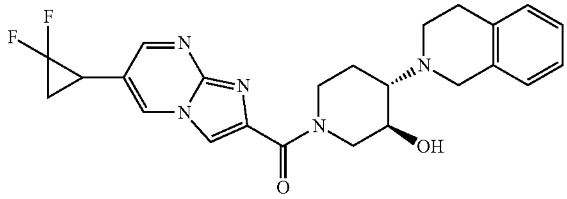 [SMILES: O=C(c1cn2cc(C3CC3(F)F)cnc2n1)N1CC[C@H](N2CCc3ccccc3C2)[C@@H](O)C1]

To a solution of DIEA (0.219 mL, 1.25 mmol), 6-(2,2-difluorocyclopropyl)imidazo[1,2-a]pyrimidine-2-carboxylic acid (100 mg, 0.418 mmol), and (3S,4S)-4-(3,4-dihydroisoquinolin-2(1H)-yl)piperidin-3-ol (117 mg, 0.502 mmol) in DMF (3 mL) was added T3P (798 mg, 1.25 mmol). The mixture was stirred at 15° C. for 2 h and then concentrated under reduced pressure. The residue was purified by reverse phase HPLC (ACN/water gradient) to give (6-(2,2-difluorocyclopropyl)imidazo[1,2-a]pyrimidin-2-yl)((3S,4S)-4-(3,4-dihydroisoquinolin-2(1H)-yl)-3-hydroxypiperidin-1-yl)methanone as a solid. MS: 454 (M+1). $^1$H NMR (500 MHz, $CD_3OD$) δ 8.88 (s, 1H), 8.65 (br s, 1H), 8.16 (s, 1H), 7.16-7.01 (m, 4H), 4.85-4.83 (m 2H), 4.03-3.79 (m, 3H), 3.26-2.71 (m, 8H), 2.15-1.89 (m, 3H), 1.80-1.70 (m, 1H).

Example 3: (6-cyclopropylimidazo[1,2-a]pyrimidin-2-yl)((3S,4S)-4-(3,4-dihydroisoquinolin-2(1H)-yl)-3-hydroxypiperidin-1-yl)methanone

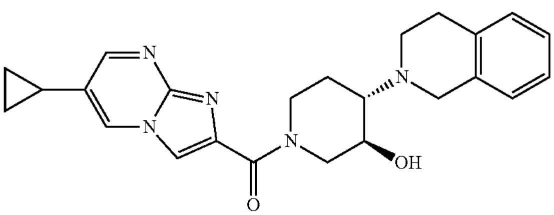 [SMILES: O=C(c1cn2cc(C3CC3)cnc2n1)N1CC[C@H](N2CCc3ccccc3C2)[C@@H](O)C1]

To a solution of 6-cyclopropylimidazo[1,2-a]pyrimidine-2-carboxylic acid (80 mg, 0.394 mmol) in DMF (4 mL) was added HATU (180 mg, 0.472 mmol), DIEA (0.206 mL, 1.181 mmol), and (3S,4S)-4-(3,4-dihydroisoquinolin-2(1H)-yl)piperidin-3-ol (91 mg, 0.394 mmol). The mixture was stirred at 15° C. for 30 min. The mixture was purified directly by reverse phase HPLC (ACN/water gradient with 0.1% TFA modifier) to give (6-cyclopropylimidazo[1,2-a]pyrimidin-2-yl)((3S,4S)-4-(3,4-dihydroisoquinolin-2(1H)-yl)-3-hydroxypiperidin-1-yl)methanone as a solid. MS: 418 (M+1). $^1$H NMR (500 MHz, CD3OD) δ 8.70 (d, J=2.1 Hz, 1H), 8.66 (d, J=2.3 Hz, 1H), 8.18 (s, 1H), 7.37-7.21 (m, 4H), 5.24-4.98 (m, 1H), 4.88-4.36 (m, 3H), 4.28-3.99 (m, 1H), 3.93-3.39 (m, 4H), 3.29-2.73 (m, 3H), 2.27 (br s, 1H), 2.14-2.06 (m, 1H), 2.05-1.90 (m, 1H), 1.19-1.07 (m, 2H), 0.92-0.79 (m, 2H).

Example 4: (6-bromo-7-ethylimidazo[1,2-a]pyrimidin-2-yl)((3S,4S)-4-(3,4-dihydroisoquinolin-2(1H)-yl)-3-hydroxypiperidin-1-yl)methanone

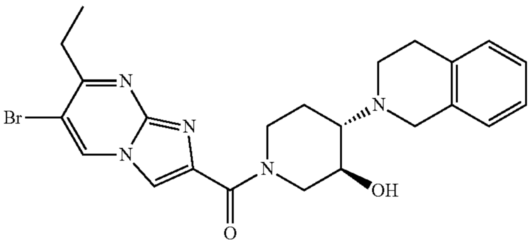

To a solution of 6-bromo-7-ethylimidazo[1,2-a]pyrimidine-2-carboxylic acid (32 mg, 0.118 mmol) in DMF (4 mL) was added HATU (54 mg, 0.142 mmol), DIEA (0.062 mL, 0.355 mmol), and (3S,4S)-4-(3,4-dihydroisoquinolin-2(1H)-yl)piperidin-3-ol (28 mg, 0.118 mmol). The mixture was stirred at 20° C. for 30 min. The mixture was purified directly by reverse phase HPLC (ACN/water gradient with 0.1% TFA modifier) to give (6-bromo-7-ethylimidazo[1,2-a]pyrimidin-2-yl)((3S,4S)-4-(3,4-dihydroisoquinolin-2(1H)-yl)-3-hydroxypiperidin-1-yl)methanone as a solid. MS: 484 and 486 (M+1). $^1$H NMR (400 MHz, CD3OD) δ 9.16 (br s, 1H), 8.15 (br s, 1H), 7.36-7.21 (m, 4H), 4.98-5.17 (m, 2H), 4.80-4.71 (m, 1H), 4.51-4.45 (m, 1H), 4.15-4.05 (m, 1H), 3.81-3.62 (m, 3H), 3.40-2.80 (m, 6H), 2.26-1.97 (m, 2H), 1.37 (t, J=7.24 Hz, 3H).

PRMT5-MEP50 Enzyme Methylation Assay

PRMT5-MEP50 biochemical assay is a direct measurement of the methylation activity of the enzyme complex on a short peptide substrate derived from the N-terminus of H4 histone. Methylation experiment was performed with recombinant PRMT5-MEP50 protein complex. The assessment of inhibitory effect of small molecules was measured by the effectiveness of the compounds to inhibit this reaction ($EC_{50}$).

In this assay, the potency ($EC_{50}$) of each compound was determined from a twenty-point (1:2 serial dilution; top compound concentration of 100000 nM) titration curve using the following outlined procedure. To each well of a white ProxiPlus 384 well-plate, 100 nL of compound (1% DMSO in final assay volume of 10 µL) was dispensed, followed by the addition of 8 µL of 1× assay buffer (50 mM Bicine pH 8.0, 1 mM DTT, 0.004% Tween20, 0.01% BSA) containing 1.25 nM of Full-length (FL)-PRMT5-MEP50 enzyme complex (recombinant proteins from baculovirus-transfected Sf21 cells: FL-PRMT5; MW=73837 kDa and FL-MEP50; MW=38614) and 1 µL of 150 µM S-(5'-Adenosyl)-L-Methionine Chloride (SAM). Plates were sealed and placed in a 37° C. humidified chamber for a 60 minutes pre-incubation with compound. Subsequently, each reaction was initiated by the addition of 1 µL 1× assay buffer containing 750 nM biotinylated H4R3(Me1) peptide. The final reaction in each well of 10 µL consists of 1.0 nM PRMT5-MEP50, 75 nM biotinylated-peptide, and 15 µM SAM. Methylation reactions were allowed to proceed for 150 minutes in a sealed plate at 37° C. Reactions were immediately quenched by the addition of 1 µL of 5% formic acid. Plates were then frozen and shipped to SAMDITM Tech Inc. to determine the percent conversion from H4R3 (Me1) to H4R3(Me2). Dose-response curves were generated by plotting percent effect (% product conversion; Y-axis) vs. Log10 compound concentrations (X-axis). $EC_{50}$ values were determined by non-linear regression according to models for sigmoidal (4 parameters) dose-response curves.

PRMT5 Cell Target Engagement (TE) Assay

The PRMT5 TE assay is a biomarker assay for identifying compounds that inhibit symmetric dimethylation of arginine (SDMA) of PRMT5 substrates. The following substrates have been reported for PRMT5: histone H2A and H4 R3, Histone H3 R2, Histone H3 R8, spliceosome Sm proteins, ribosomal protein RPS10, p53, FEN1, nucleoplasmin, nucleolin, EGFR and EBNA. The assay focuses on detecting symmetrically dimethylated nuclear proteins using high content imaging technology. Detection of the expression of symmetrically dimethylated nuclear proteins is through a mixture of primary rabbit monoclonal antibodies to SDMA (CST 13222), which in turn recognized by an Alexafluor 488 dye-conjugated anti-rabbit IgG secondary antibody. The IN Cell Analyzer 2200 or Opera-Phenix measures nuclear Alexafluor 488 fluorescent dye intensity that is directly related to the level of expression of symmetrically dimethylated nuclear proteins at the single cell level. Nuclear AF488 dye intensities are compared to the mean value for DMSO treated cells (MIN) to report percent of inhibition for each compound-treated well.

In this assay, the cell potency ($EC_{50}$) of each compound was determined from a ten point (1:3 serial dilution; top compound concentration of 10000 nM) titration curve using the following outlined procedure. Each well of a BD falcon collagen coated black/clear bottom 384-well plate was seeded with 4000 MCF-7 cells in 30 µl media and allowed to attach for 5 h. Media is ATCC-formulated Eagle's Minimum Essential Medium, Catalog No. 30-2003. To make the complete growth medium, the following components were added to the base medium: 0.01 mg/mL human recombinant insulin; fetal bovine serum to a final concentration of 10%. Additional 30 □l of media containing 2× compounds were added to each well. Cells were treated for 3 days in 37° C. $CO_2$ incubator. On day 3, cells were fixed with Cytofix, permeabilized with 0.4% Triton-X-100/Cytofix, and washed with D-PBS without Ca/Mg. Cells were blocked with Licor Odessey blocking reagent for 1 h at room temperature, followed by incubation with anti-SDMA (1:1000) antibody at 4° C. overnight. 1° antibody was removed, followed by three washings with DPBS without Ca/Mg and 0.05% Tween20. Hoechst (5 µg/mL), Cell Mask deep stain (1:2000) and Alexa488-conjugated goat anti-rabbit IgG (2 µg/mL) was added for 1 h at room temperature. A final washing step (three washes) was performed before sealing plate for imaging on In Cell Analyzer 2200 or Opera-Phenix. Images from analyzer were uploaded to Columbus (at WP or BOS) for image analysis. $IC_{50}$ values were determined by 4 parameters robust fit of percent fluorescence units vs. ($Log_{10}$) compound concentrations.

Representative compounds of the present invention were tested using the assay protocol described in this example. Results are provided in Table 2 below.

TABLE 2

| Ex. No. | Enzyme Methylation Assay ($EC_{50}$, nM) | TE Assay ($EC_{50}$, nM) |
|---|---|---|
| 1 | 0.9 | 6.9 |
| 1b | 0.9 | 2 |
| 1c | 49; 9772 | 165 |
| 2 | 1.6 | 4.7 |
| 3 | 1.3 | 6.8 |
| 4 | 1.5 | 15 |

What is claimed is:

1. A compound selected from:

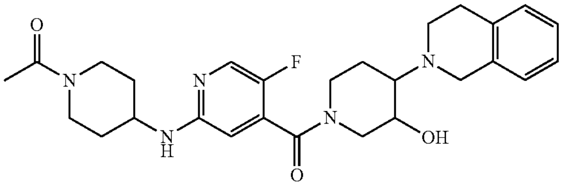
,

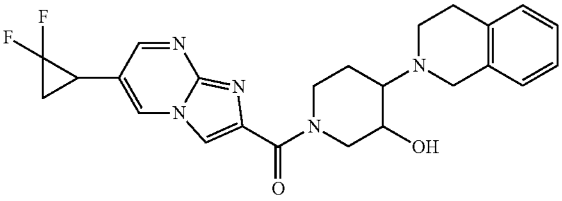
,

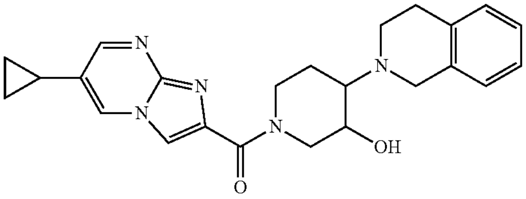
, and

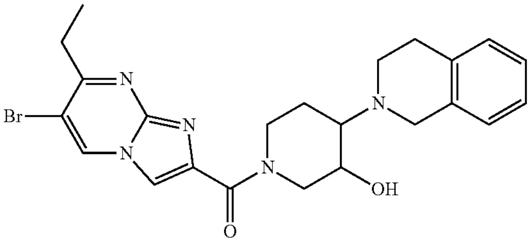
, or a pharmaceutically acceptable salt thereof.

2. A compound of claim 1 selected from:

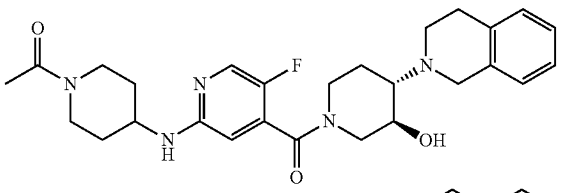

,

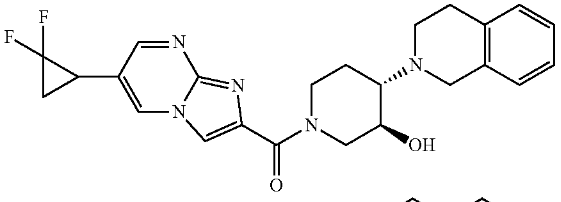

,

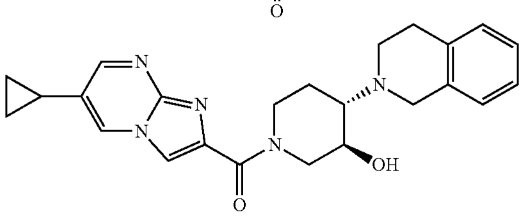

, and

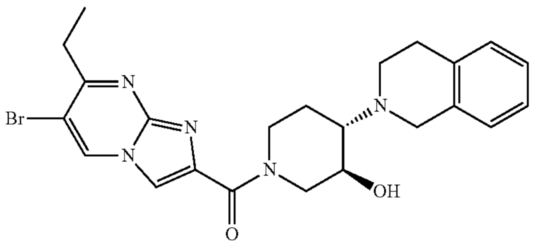 [SMILES: CCc1nc2nc(C(=O)N3CC[C@H](N4CCc5ccccc5C4)[C@@H](O)C3)cn2cc1Br]

, or a pharmaceutically acceptable salt thereof.

3. A compound of claim 1, which is:

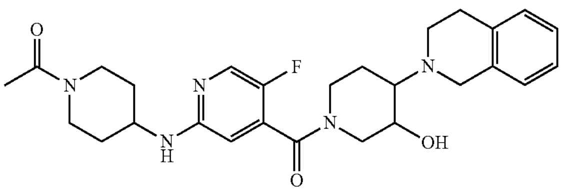

, or a pharmaceutically acceptable salt thereof.

4. A compound of claim 1, which is:

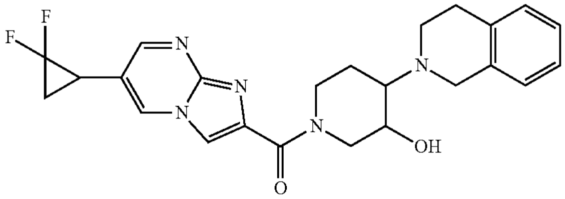

, or a pharmaceutically acceptable salt thereof.

5. A compound of claim 1, which is:

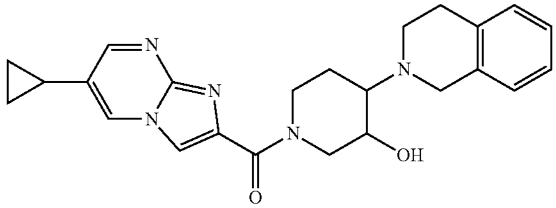

, or a pharmaceutically acceptable salt thereof.

6. A compound of claim 1, which is:

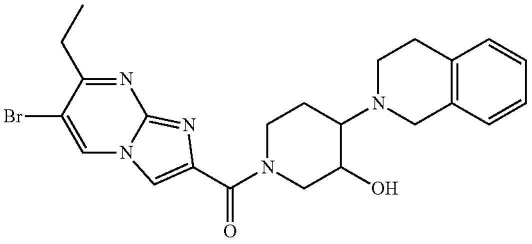

, or a pharmaceutically acceptable salt thereof.

7. The compound of claim 1, which is: 1-{4-[(4-{[(3S, 4S)-4-(3,4-dihydroisoquinolin-2(1H)-yl)-3-hydroxypiperidin-1-yl]carbonyl}-5-fluoropyridin-2-yl)amino]piperidin-1-yl}ethanone or a pharmaceutically acceptable salt thereof.

8. The compound of claim 1, which is: (6-(2,2-difluorocyclopropyl)imidazo[1,2-a]pyrimidin-2-yl)((3S,4S)-4-(3,4-dihydroisoquinolin-2(1H)-yl)-3-hydroxypiperidin-1-yl) methanone, or a pharmaceutically acceptable salt thereof.

9. The compound of claim 1, which is: (6-cyclopropylimidazo[1,2-a]pyrimidin-2-yl)((3S,4S)-4-(3,4-dihydroisoquinolin-2(1H)-yl)-3-hydroxypiperidin-1-yl)methanone, or a pharmaceutically acceptable salt thereof.

10. The compound of claim 1, which is: (6-bromo-7-ethylimidazo[1,2-a]pyrimidin-2-yl)((3S,4S)-4-(3,4-dihydroisoquinolin-2(1H)-yl)-3-hydroxypiperidin-1-yl)methanone, or a pharmaceutically acceptable salt thereof.

11. A pharmaceutical composition comprising a compound of claim 1, or a pharmaceutically acceptable salt thereof, and a pharmaceutically acceptable carrier.

12. The method for treating cancer comprising administering to a patient in need thereof a compound of claim 1, or a pharmaceutically acceptable salt thereof.

13. The method for treating sickle cell disease comprising administering to a patient in need thereof a compound of claim 1, or a pharmaceutically acceptable salt thereof.

14. The method for treating hereditary persistence of foetal hemoglobin (HPFH) mutations comprising administering to a patient in need thereof a compound of claim 1, or a pharmaceutically acceptable salt thereof.

* * * * *